US012680105B2

(12) United States Patent
Kassiotis et al.

(10) Patent No.: US 12,680,105 B2
(45) Date of Patent: Jul. 14, 2026

(54) CANCER ANTIGENS AND METHODS

(71) Applicants:Enara Bio Limited, Oxford (GB); The Francis Crick Institute Limited, London (GB)

(72) Inventors: George Kassiotis, London (GB); George Young, London (GB); Jan Attig, London (GB); Fabio Marino, Oxford (GB)

(73) Assignees: Enara Bio Limited, Oxford (GB); The Francis Crick Institute Limited, London (GB)

( * ) Notice: Subject to any disclaimer, the term of this patent is extended or adjusted under 35 U.S.C. 154(b) by 1161 days.

(21) Appl. No.: 17/644,931

(22) Filed: Dec. 17, 2021

(65) Prior Publication Data

US 2022/0211760 A1 Jul. 7, 2022

Related U.S. Application Data

(63) Continuation of application No. PCT/GB2020/051594, filed on Jul. 3, 2020.

(30) Foreign Application Priority Data

Jul. 5, 2019 (EP) ..................................... 19184742

(51) Int. Cl.
| | |
|---|---|
| *C12N 15/63* | (2006.01) |
| *A61K 40/11* | (2025.01) |
| *A61K 40/17* | (2025.01) |
| *A61K 40/24* | (2025.01) |
| *A61K 40/32* | (2025.01) |
| *A61K 40/42* | (2025.01) |
| *A61K 40/46* | (2025.01) |
| *A61P 35/00* | (2006.01) |
| *C12N 5/0783* | (2010.01) |
| *C12N 5/0784* | (2010.01) |

(52) U.S. Cl.
CPC .............. *C12N 15/63* (2013.01); *A61K 40/11* (2025.01); *A61K 40/17* (2025.01); *A61K 40/24* (2025.01); *A61K 40/32* (2025.01); *A61K 40/42* (2025.01); *A61K 40/4201* (2025.01); *A61K 40/4272* (2025.01); *A61K 40/46* (2025.01); *A61P 35/00* (2018.01); *C12N 5/0638* (2013.01); *C12N 5/0639* (2013.01); *A61K 2239/57* (2023.05)

(58) Field of Classification Search
None
See application file for complete search history.

(56) References Cited

U.S. PATENT DOCUMENTS

| | | | |
|---|---|---|---|
| 6,566,325 B2 | 5/2003 | Moore et al. | |
| 7,504,490 B1 | 3/2009 | Weinstock et al. | |
| 7,745,391 B2 | 6/2010 | Mintz et al. | |
| 11,666,644 B2 | 6/2023 | Lisziewicz et al. | |
| 12,263,216 B2 | 4/2025 | Kassiotis et al. | |
| 2002/0082206 A1 | 6/2002 | Leach et al. | |
| 2007/0072175 A1 | 3/2007 | Cooper et al. | |
| 2007/0083334 A1 | 4/2007 | Mintz et al. | |
| 2010/0136518 A1 | 6/2010 | Humer et al. | |
| 2010/0285509 A1 | 11/2010 | Mayer et al. | |
| 2011/0183924 A1 | 7/2011 | Mintz et al. | |
| 2011/0217326 A1 | 9/2011 | Kudo et al. | |
| 2014/0099324 A1 | 4/2014 | Wang-Johanning | |
| 2015/0119265 A1 | 4/2015 | Perot et al. | |
| 2016/0160295 A1 | 6/2016 | Chinnaiyan et al. | |
| 2018/0015975 A1* | 1/2018 | Fritsch et al. ..... | A61K 39/0011 |
| 2019/0322721 A1 | 10/2019 | Sonntag et al. | |
| 2019/0351040 A1 | 11/2019 | Valiente et al. | |
| 2021/0353729 A1 | 11/2021 | Kassiotis et al. | |
| 2022/0211760 A1 | 7/2022 | Kassitois et al. | |
| 2022/0213159 A1 | 7/2022 | Kassiotis et al. | |
| 2022/0218807 A1 | 7/2022 | Kassiotis et al. | |
| 2022/0220175 A1 | 7/2022 | Kassiotis et al. | |
| 2023/0167163 A1 | 6/2023 | Kassiotis et al. | |
| 2023/0302109 A1 | 9/2023 | Kassiotis et al. | |
| 2024/0156932 A1 | 5/2024 | Davies et al. | |

FOREIGN PATENT DOCUMENTS

| | | | | |
|---|---|---|---|---|
| EP | 1580263 | A1 | 9/2005 | |
| EP | 2878678 | A1 | 6/2015 | |
| JP | 2003304877 | A | 10/2003 | |
| TW | 1658050 | * | 5/2019 | .............. A61P 35/00 |
| WO | WO-2000006598 | A1 | 2/2000 | |
| WO | 2001064835 | A2 | 9/2001 | |
| WO | 200175067 | A2 | 10/2001 | |
| WO | WO-2001077330 | A2 | 10/2001 | |
| WO | 2004038003 | A2 | 5/2004 | |

(Continued)

OTHER PUBLICATIONS

Nagata et al., "Synthesis and biological activity of artificial mRNA prepared with novel phosphorylating agents" Nucleic Acid Res ( Year: 2010).*

Nagata et al., "Synthesis and biological activity of artificial mRNA prepared with novel phosphyerlating agents" Nucleic Acid Res. ( Year: 2010).*

Luan et al., "Engineering exosomes as refined biological nanoplatforms for drug delivery" (Year: 2017).*

Pandiani, Charlotte, et al. "Focus on cutaneous and uveal melanoma specificities." Genes & development 31.8 (2017): 724-743.

"Acetyltransferase," EBI Accession No. UNIPROT: D6AHI5.

Attermann et al., "Human endogenous retroviruses and their implication for immunotherapeutics of cancer," Ann Oncol. Nov. 1, 2018;29(11):2183-2191.

Attig et al., "Physiological and Pathological Transcriptional Activation of Endogenous Retroelements Assessed by RNA-Sequencing of B Lymphocytes," Front Microbiol. Dec. 12, 2017;8:2489.

(Continued)

*Primary Examiner* — Tracy Vivlemore
*Assistant Examiner* — John David Moore
(74) *Attorney, Agent, or Firm* — COOLEY LLP; Andrew T. Wilkins; Jennifer Mandal

(57) ABSTRACT

There are disclosed inter alia polypeptides and nucleic acids encoding said polypeptides which are useful in the treatment, prevention and diagnosis of cancer, particularly non small cell lung cancer, especially lung squamous cell carcinoma and melanoma, especially cutaneous melanoma.

20 Claims, 7 Drawing Sheets

Specification includes a Sequence Listing.

(56) References Cited

FOREIGN PATENT DOCUMENTS

| WO | WO-2005099750 A1 | 10/2005 |
| WO | 2006105642 A1 | 10/2006 |
| WO | WO-2006103562 A2 | 10/2006 |
| WO | WO-2006119527 A2 | 11/2006 |
| WO | 2007073478 A2 | 6/2007 |
| WO | WO-2007109583 A2 | 9/2007 |
| WO | WO-2007137279 A2 | 11/2007 |
| WO | WO-2008016356 A2 | 2/2008 |
| WO | 2008118258 A2 | 10/2008 |
| WO | WO-2009026116 A2 | 2/2009 |
| WO | WO-2009039244 A2 | 3/2009 |
| WO | 2013033333 A1 | 3/2013 |
| WO | 2013040142 A2 | 3/2013 |
| WO | 2013041142 A1 | 3/2013 |
| WO | 2014004385 A2 | 1/2014 |
| WO | 2017097602 A1 | 6/2017 |
| WO | WO-2017097699 A1 | 6/2017 |
| WO | 2019133934 A2 | 7/2019 |
| WO | WO-2020079448 A1 | 4/2020 |
| WO | 2020257922 A1 | 12/2020 |
| WO | WO-2020260897 A1 | 12/2020 |
| WO | WO-2020260898 A2 | 12/2020 |
| WO | 2021005338 A2 | 1/2021 |
| WO | 2021005339 A1 | 1/2021 |
| WO | 2021209775 A1 | 10/2021 |
| WO | 2021212123 A1 | 10/2021 |
| WO | 2022229647 A1 | 11/2022 |
| WO | 2023230573 A2 | 11/2023 |
| WO | 2025133007 A1 | 6/2025 |

OTHER PUBLICATIONS

Attig et al., "LTR retroelement expansion of the human cancer transcriptome and immunopeptidome revealed by de novo transcript assembly," Genome Res. Oct. 2019;29(10):1578-1590(supplemental materials).

Bannert et al., "HERVs new role in cancer: from accused perpetrators to cheerful protectors," Front Microbiol. Feb. 13, 2018;9:178.

Cegolon et al., "Human endogenous retroviruses and cancer prevention: evidence and prospects," BMC Cancer. Jan. 3, 2013;13:4.

Escudier et al., "Vaccination of metastatic melanoma patients with autologous dendritic cell (DC) derived-exosomes: results of thefirst phase I clinical trial," J Transl Med. Mar. 2, 2005;3:10.

Ferrucci et al., "Newly identified tumor antigens as promising cancer vaccine targets for malignant melanoma treatment," Curr Top Med Chem. 2012;12(1):11-31.

"*Homo sapiens* isolate KOREF chromosome 18 KOREF.98780, whole genome shotgun sequence," EBI Accession No. LWKW01098780.

"*Homo sapiens* isolate KOREF chromosome 13 KOREF.81120, whole genome shotgun sequence," EBI Accession No. LWKW01081120.

Jayson et al., "Ovarian cancer," Lancet. Oct. 11, 2014;384(9951):1376-88.

"Macaca fuscata fuscata DNA, clone: MSB2-228H05_R, genomic survey sequence," EBI Accession No. AG759599.

PCT International Search Report and Written Opinion from PCT/GB2021/050940, dated Aug. 3, 2021.

PCT International Search Report and Written Opinion from PCT/US2021/028029, dated Aug. 9, 2021.

Schuster et al., "The immunopeptidomic landscape of ovarian carcinomas," Proc Natl Acad Sci U S A. Nov. 14, 2017;114(46):E9942-E9951.

"UI-H-DPO-avc-g-14-0-UI.s1 NCI_CGAP_Fs1 *Homo sapiens* cDNA clone UI-H-DPO-avc-g-14-0-UI 3', mRNA sequence," EBI Accession No. CA441646.

UniParc—UPI00060150B7.

Yin et al., "Immature dendritic cell-derived exosomes: a promise subcellular vaccine for autoimmunity," Inflammation. Feb. 2013;36(1):232-40.

Attig et al., Supplemental Material—"LTR retroelement expansion of the human cancer transcriptome and immunopeptidome revealed by de novo transcript assembly," Genome Res. Oct. 2019;29(10): (160 pages).

Acha-Orbea and MacDonald, "Superantigens of mouse mammary tumor virus," Annu Rev Immunol. 1995;13:459-86.

Andersson et al., "Expression of human endogenous retrovirus ERV3 (HERV-R) mRNA in normal and neoplastic tissues," Int J Oncol. Feb. 1998;12(2):309-13.

Attig et al., "LTR retroelement expansion of the human cancer transcriptome and immunopeptidome revealed by de novo transcript assembly," Genome Res. Oct. 2019;29(10):1578-1590.

Aung et al., "Expression of NY-ESO-1 in primary and metastatic melanoma," Hum Pathol. Feb. 2014;45(2):259-67.

Babaian and Mager, "Endogenous retroviral promoter exaptation in human cancer," Mob DNA. Dec. 1, 2016;7:24.

Bassani-Sternberg et al., "Direct identification of clinically relevant neoepitopes presented on native human melanoma tissue by mass spectrometry," Nat Commun. Nov. 21, 2016;7:13404.

Bulik-Sullivan et al., "Deep learning using tumor HLA peptide mass spectrometry datasets improves neoantigen identification," Nat Biotechnol. Jan. 2019;37(1):55-63.

Cherkasova et al., "Endogenous retroviruses as targets for antitumor immunity in renal cell cancer and other tumors," Front Oncol. Sep. 17, 2013;3:243.

Gigoux and Wolchok, "Refusing to TAP out: 16 new human TEIPPs identified," J Exp Med. Sep. 3, 2018;215(9):2233-2234.

Hoyos and Abdel-Wahab, "Cancer-specific splicing changes and the potential for splicing-derived neoantigens," Cancer Cell. Aug. 13, 2018;34(2):181-183.

Humer et al., "Identification of a melanoma marker derived from melanoma-associated endogenous retroviruses," Cancer Res. Feb. 1, 2006;66(3):1658-63.

Hurst and Magiorkinis, "Activation of the innate immune response by endogenous retroviruses," J Gen Virol. Jun. 2015;96(Pt 6):1207-1218.

Kahles et al., "Comprehensive analysis of alternative splicing across tumors from 8,705 patients," Cancer Cell. Aug. 13, 2018;34(2):211-224.e6.

Kassiotis and Stoye, "Immune responses to endogenous retroelements: taking the bad with the good," Nat Rev Immunol. Apr. 2016;16(4):207-19.

Katoh and Kurata, "Association of endogenous retroviruses and long terminal repeats with human disorders," Front Oncol. Sep. 11, 2013;3:234.

Kershaw et al., "Immunization against endogenous retroviral tumor-associated antigens," Cancer Res. Nov. 1, 2001;61(21):7920-4.

Laumont et al., "Noncoding regions are the main source of targetable tumor-specific antigens," Sci Transl Med. Dec. 5, 2018;10(470):eaau5516.

Lauss et al., "Mutational and putative neoantigen load predict clinical benefit of adoptive T cell therapy in melanoma," Nat Commun. 2017;8:1738.

Lock et al., "Distinct isoform of FABP7 revealed by screening for retroelement-activated genes in diffuse large B-cell lymphoma," Proc Natl Acad Sci U S A. Aug. 26, 2014;111(34):E3534-43.

Mangeney et al., "The full-length envelope of an HERV-H human endogenous retrovirus has immunosuppressive properties," J Gen Virol. Oct. 2001;82(Pt 10):2515-2518.

Marijt et al., "Identification of non-mutated neoantigens presented by TAP-deficient tumors," J Exp Med. Sep. 3, 2018;215(9):2325-2337.

Ribas and Wolchok, "Cancer immunotherapy using checkpoint blockade," Science. Mar. 23, 2018;359(6382):1350-1355.

Ruprecht et al., "Endogenous retroviruses," Cell Mol Life Sci. Nov. 2008;65(21):3366-82.

Sacha et al., "Vaccination with cancer-and HIV infection-associated endogenous retrotransposable elements is safe and immunogenic," J Immunol. Aug. 1, 2012;189(3):1467-79.

Schiavetti et al., "A human endogenous retroviral sequence encoding an antigen recognized on melanoma by cytolytic T lymphocytes," Cancer Res. Oct. 1, 2002;62(19):5510-6.

(56) References Cited

OTHER PUBLICATIONS

DNA fragments of a human Tox gene, 47247, EBI Accession No. GSN: ARC03196 (1 page).

Human derived non-coding RNA MEAT62.1, SEQ:1895, EBI Accession No. GSN: BCQ58603 (1 page).

Sequence Aspergillus fumigatus ORF amino acid sequence SEQ ID No. 31732, EBI Accession No. GSP: AWP60286 (1 page).

Sequence Human ORF553, Ebi Accession No. GSP: ABP64183 (1 page).

Sequence Human derived non-coding RNA CAT2186.2 SEQ: 1274, EBI accession No. GSN: BCQ57982 (2 pages).

Sequence SubName: Full = Acetyltransferase, EBI Accession No. UNIPROT: D6AHI5 (1 page).

Slansky et al., "Enhanced antigen-specific antitumor immunity with altered peptide ligands that stabilize the MHC-peptide-TCR complex," Immunity. Oct. 2000;13(4):529-38.

Smart et al., "Intron retention is a source of neoepitopes in cancer" Nat Biotechnol. Dec. 2018;36(11):1056-1058.

Ternette et al., "Immunopeptidomic Profiling of HLA-A2-Positive Triple Negative Breast Cancer Identifies Potential Immunotherapy Target Antigens," Proteomics. Jun. 2018;18(12):e1700465.

Wang-Johanning et al., "Detecting the expression of human endogenous retrovirus E envelope transcripts in human prostate adenocarcinoma," Cancer. Jul. 1, 2003;98(1):187-97.

Wold and Toth, "Adenovirus vectors for gene therapy, vaccination and cancer gene therapy," Curr Gene Ther. Dec. 2013;13(6):421-33.

Yossef et al., "Enhanced detection of neoantigen-reactive T cells targeting unique and shared oncogenes for personalized cancer immunotherapy," JCI Insight. Oct. 4, 2018;3(19):e122467.

"Pricing and Ordering—Commercial", Proteomics International, Retrieved from: https://www.proteomics.com.au/analytical-services/pricing-and-ordering/, Apr. 1, 2014, 7 pages.

Abbott et al., "Abstract 312: Identification of novel non-small cell lung cancer (NSCLC) Dark Antigens (TM), with expression in multiple tumor types, as promising targets for immunotherapies", Retrieved from: https://jitc.bmj.com/content/jitc/10/Suppl_2/A328.full.pdf, Journal of Immunotherapy of Cancer, 2022, 10(Suppl 2):A328.

Abbott et al., "Abstract 343: Identification of Tumor-Reactive T Cells Targeting Melanoma Dark Antigens(TM) Validates This Novel Class of Targets For Development of Immunotherapies", Retrieved from: https://jitc.bmj.com/content/jitc/10/Suppl_2/A361.full.pdf, Journal of Immunotherapy of Cancer, 2022, 10(Suppl 2):A361.

Abbott et al., "Identification of novel non-small cell lung cancer (NSCLC) Dark Antigens (TM), with expression in multiple tumor types, as promising targets for immunotherapies", Retrieved from: https://enarabio.ams3.cdn.digitaloceanspaces.com/EnaraBio-312-SITC-2022-Poster.pdf, The Society for Immunology of Cancers, 37th Annual Meeting, SITC, 2022, 1 page.

Finney et al., "Germinal center responses to complex antigens", Immunological Reviews, 2018, 284(1):42-50.

Lin et al., "Melanoma-associated antigens in esophageal adenocarcinoma: Identification of novel MAGE-A10 splice variants", Journal of the American College of Surgeons, 2004, 199(3):S32.

Matsuzaki et al., "Systematic Identification of Human Melanoma Antigens Using Serial Analysis of Gene Expression (SAGE)", Journal of Immunotherapy, Jan./Feb. 2005, 28(1):10-19.

Nelde et al., "The Peptide Vaccine of the Future", Molecular Cell Proteomics, 2021, 20:100022, pp. 1-11.

Paul et al., "HLA class I alleles are associated with peptide-binding repertoires of different size, affinity, and immunogenicity", The Journal of Immunology, Dec. 15, 2013, 191(12):5831-5839.

Sela-Culang et al., "The structural basis of antibody-antigen recognition", Frontiers in Immunology, Oct. 2013, 4 (Article 302), pp. 1-13.

Zhao et al., "Proteogenomics uncovers a vast repertoire of shared tumor-specific antigens in ovarian cancer", Cancer Immunology Research, Apr. 2020, 8(4):544-555.

Zitvogel et al., "Eradication of established murine tumours using a novel cell-free vaccine: dendritic cell-derived exosomes", Nature Medicine, May 1998, 4(5):594-600.

International Preliminary Report on Patentability received for PCT Application No. PCT/GB2019/052980, mailed on Jan. 29, 2021, 7 pages.

International Preliminary Report on Patentability received for PCT Application No. PCT/GB2020/051557, mailed on Dec. 10, 2021, 10 pages.

International Preliminary Report on Patentability received for PCT Application No. PCT/GB2020/051558, mailed on Jan. 6, 2022, 15 pages.

International Preliminary Report on Patentability received for PCT Application No. PCT/GB2020/051592, mailed on Oct. 19, 2021, 8 pages.

International Preliminary Report on Patentability received for PCT Application No. PCT/GB2020/051594, mailed on Jan. 20, 2022, 10 pages.

International Preliminary Report on Patentability received for PCT Application No. PCT/GB2021/050940, completed on Jun. 24, 2022, 11 pages.

International Preliminary Report on Patentability received for PCT Application No. PCT/GB2022/051086, mailed on Jul. 19, 2023, 8 pages.

International Preliminary Report on Patentability received for PCT Application No. PCT/US2021/028029, mailed on Jul. 13, 2022, 15 pages.

International Search Report and Written Opinion received for PCT Application No. PCT/EP2024/087738, mailed on Jun. 3, 2025, 19 pages.

International Search Report and Written Opinion received for PCT Application No. PCT/GB2019/052980, mailed on Apr. 20, 2020, 21 pages.

International Search Report and Written Opinion received for PCT Application No. PCT/GB2020/051557, mailed on Sep. 22, 2020, 11 pages.

International Search Report and Written Opinion received for PCT Application No. PCT/GB2020/051558, mailed on Dec. 23, 2020, 19 pages.

International Search Report and Written Opinion received for PCT Application No. PCT/GB2020/051592, mailed on Jan. 18, 2021, 22 pages.

International Search Report and Written Opinion received for PCT Application No. PCT/GB2020/051594, mailed on Sep. 16, 2020, 13 pages.

International Search Report and Written Opinion received for PCT Application No. PCT/GB2022/051086, mailed on Aug. 19, 2022, 19 pages.

U.S. Appl. No. 62/866,089.

U.S. Appl. No. 19/062,913, Kassiotis et al., filed Feb. 25, 2025.

U.S. Appl. No. 19/249,526, Kundu et al., filed Jun. 25, 2025.

* cited by examiner

Lung Tumor

Synthetic

Melanoma tumor

Synthetic

SEQUENCE LISTING

<160> NUMBER OF SEQ ID NOS: 8

<210> SEQ ID NO 1
<211> LENGTH: 40
<212> TYPE: PRT
<213> ORGANISM: Homo sapiens

<400> SEQUENCE: 1

Met Gly Gln Leu Asn Asn Leu Ile Ser Ile Met Ser Ser Ser Arg Ile
1               5                   10                  15

Leu Glu Val Val Arg Gln Pro Lys Trp Lys Gly Ser Arg Arg Gly Ile
            20                  25                  30

Leu Val Leu Pro Ile Thr His Met
        35                  40

<210> SEQ ID NO 2
<211> LENGTH: 88
<212> TYPE: PRT
<213> ORGANISM: Homo sapiens

<400> SEQUENCE: 2

```
Met Pro Cys Pro Ala Ser Ala His Thr Arg Cys Val His Pro Leu Thr
1               5                   10                  15

Cys Ala His Cys Leu Ala Leu Pro Ser Glu Met His Pro Val Pro Gln
            20                  25                  30

Met Glu Met Gln Lys Ser Pro Val Phe Cys Val Ala His Ala Gly Ser
        35                  40                  45

Cys Arg Pro Glu Leu Phe Leu Phe Ser His Leu Gly Ser Ser Ser Gln
        50                  55                  60

Ser Thr Ile Leu Phe Ser Leu Leu Ile Leu Ser Asp Met His Thr Lys
65                  70                  75                  80

His Thr Val Asp Leu Glu Asn Gly
                85

<210> SEQ ID NO 3
<211> LENGTH: 10
<212> TYPE: PRT
<213> ORGANISM: Homo sapiens

<400> SEQUENCE: 3

Arg Ile Leu Glu Val Val Arg Gln Pro Lys
1               5                   10

<210> SEQ ID NO 4
<211> LENGTH: 10
<212> TYPE: PRT
<213> ORGANISM: Homo sapiens

<400> SEQUENCE: 4

Leu Ser Asp Met His Thr Lys His Thr Val
1               5                   10

<210> SEQ ID NO 5
<211> LENGTH: 395
<212> TYPE: DNA
<213> ORGANISM: Homo sapiens

<400> SEQUENCE: 5
gaaagacagc attcaaggaa ccaccttgta cgcagacact gaaacctcgc gagacaacaa        60
aactgctgac accttgatct tggacttccc agcctccaga actataaacc agcaaagagt       120
acatagaaca aacatttttt ttagaaggat taaatgggac aattaaacaa tttgatcagc       180
ataatgtcca gctcaaggat cttggaggtg gtgaggcagc ccaagtggaa aggcagcaga       240
aggggtatcc ttgttttacc aattactcat atgtaggaga tggtgcatta aatgaaatat       300
tctctgctct ctcctaacat ctacccctc acaccaagag gaaggcatgt cgcctgaacc        360
tttgcagtat tcaattaaag ttctattcac acggt                                  395

<210> SEQ ID NO 6
<211> LENGTH: 1763
<212> TYPE: DNA
<213> ORGANISM: Homo sapiens

<400> SEQUENCE: 6
ttcgagcttc ccagctgctt tgtttaccta agcaagcctg ggcaatggtg ggcgtccctc        60
ccccagcctc gctgccgcct tgcagtttga tctcagactg ctgtgctagc aatcagcgag       120
actccgtggg cgtaggaccc tccgagccag gtgcgggata taatcttgtg gtgcgctgtt       180
ttttaagccg gtcggaaaag cgcagtattc gggtgggagt gacctgattt ccaggtgcg        240
```

```
tccgtcaccc ctttctttga ctcggaaagg gaactccctg accccttgcg cttcccaagt      300
gaggcaatgc cttgcccggc ttcggctcac acacggtgtg tgcacccact gacctgcgcc      360
cactgtctgg cactccctag tgagatgcac ccggtacctc agatggaaat gcagaaatca      420
cccgtcttct gcgtcgctca cgctgggagc tgtagaccgg agctgttcct attcagccat      480
cttggctcct cctcccagtc caccattctt ttcagcttgc tgattctgag tgatatgcat      540
acaaagcata cagttgactt ggaaaatggc tgaagccctc actgggggaa acatcaaagg      600
aatactcact gtttatactt gaagtgaacc aacatcaact tgaatcaatg gattttgggt      660
ctgtggactg actcagatct agaaactgca cgaagaagag caattttgca tgtggcatct      720
gatatcaacc ttctgataac caagagctag tttttaatca taataaaatt gaagaatagc      780
aagttgacta cccatctatc ttacccctga gaacaccatg gcctgttttc agttgtcata      840
gattcctggg cagtaagaca ttgtgatttc cattccagcc ttgctgcaca tcatattaat      900
tatggttaag ggctcagtgt tgccatgtgg cctctggcat tccagaatct caacatccac      960
attgatatta tacagcccag ttccatggaa gaatagagca ttgaccccaa tctacagaca     1020
gcagccactg ctaagcctct caaagatact agtgtttcca tcactagcac attacttaat     1080
agagtgcctt tcgttgctcc ttgtatacat ggatgtacag tcagttgatg ggttttcacg     1140
tcttgcactg taattcaatg ctaatccctt aaacttactt ttttgtacta tgtcaagaca     1200
gttcgggtat ctctacctgg gttacagtag gctatcaacc ttcacggagc catcccaagc     1260
aaatattagc actggctcta ggtagccttg ccagaatgtt aaatttcagt taagtatgct     1320
aaatgaatgt gataacttta tgcaactttt catccatgac tttctttag tgtaaaggag     1380 caattgatta ttaggacaac tgattaactc tggttaaggt gaatagattt actaaaaaca     1440
ttgtattaat gttaatattc tcattttgtt ttaattgtgc tataattgtg taagagaatg     1500
actttgattt taggaaatat acactgaagt atttagggtt aaatggtatt atgtctccaa     1560
cttaatctca ggcagttaag aaaaattaat gtgcatgtgt gtgtgtaggg aaagaaagag     1620
ggaggaaagg aggaatagag aggaagagag agggtaaatg ataaagcaat gtggtaaaaa     1680
cattaacatt ctaacatatt gggaatctgg agattctctg taccatttc caacccatgt     1740 taagtgtgaa attacgtcaa agt                                            1763
```

```
<210> SEQ ID NO 7
<211> LENGTH: 123
<212> TYPE: DNA
<213> ORGANISM: Homo sapiens

<400> SEQUENCE: 7
atgggacaat taaacaattt gatcagcata atgtccagct caaggatctt ggaggtggtg       60
aggcagccca agtggaaagg cagcagaagg ggtatccttg ttttaccaat tactcatatg      120
tag                                                                    123
```

```
<210> SEQ ID NO 8
<211> LENGTH: 267
<212> TYPE: DNA
<213> ORGANISM: Homo sapiens

<400> SEQUENCE: 8
atgccttgcc cggcttcggc tcacacacgg tgtgtgcacc cactgacctg cgcccactgt       60
ctggcactcc ctagtgagat gcaccccggta cctcagatag aaatgcagaa atcacccgtc      120
ttctgcgtcg ctcacgctgg gagctgtaga ccggagctgt tcctattcag ccatcttggc      180
```

-continued

```
tcctcctccc agtccaccat tcttttcagc ttgctgattc tgagtgatat gcatacaaag      240
catacagttg acttggaaaa tggctga                                          267
```

CANCER ANTIGENS AND METHODS

CROSS REFERENCE

This is a Continuation Application of PCT/GB2020/051594 filed Jul. 3, 2020, which claims priority to EP 19184742.5 filed Jul. 5, 2019, the contents of each of which are hereby incorporated by reference in their entirety.

SEQUENCE LISTING

The sequence listing attached herewith, named "Enara_187346_Sequence_Listing.txt" (size 5.43 KB) and created on Jul. 3, 2020, is herein incorporated by reference it its entirety.

Field of the Invention

The present invention relates to antigenic polypeptides and corresponding polynucleotides for use in the treatment or prevention of cancer, in particular for use in treating or preventing non small cell lung cancer (NSCLC), e.g. lung squamous cell carcinoma (LUSC) and melanoma, particularly cutaneous melanoma. The present invention further relates inter alia to pharmaceutical and immunogenic compositions comprising said nucleic acids and polypeptides, immune cells loaded with and/or stimulated by said polypeptides and polynucleotides, antibodies specific for said polypeptides and cells (autologous or otherwise) genetically engineered with molecules that recognize said polypeptides.

Background of the Invention

As part of normal immunosurveillance for pathogenic microbes, all cells degrade intracellular proteins to produce peptides that are loaded onto Major Histocompatibility Complex (MHC) Class I molecules that are expressed on the surface of all cells. Most of these peptides, which are derived from the host cell, are recognized as self, and remain invisible to the adaptive immune system. However, peptides that are unique to foreign (non-self), are capable of stimulating the expansion of naïve CD8+ T cells that encode a T cell receptor (TCR) that tightly binds the MHC I-peptide complex. This expanded T cell population can produce effector CD8+ T cells (including cytotoxic T-lymphocytes—CTLs) that can eliminate the foreign antigen-tagged cells, as well as memory CD8+ T cells that can be re-amplified when the foreign antigen-tagged cells appear later in the animal's life.

MHC Class II molecules, whose expression is normally limited to professional antigen-presenting cells (APCs) such as dendritic cells (DCs), are usually loaded with peptides which have been internalised from the exogenous environment. Binding of a complementary TCR from a naïve CD4+ T cell to the MHC II-peptide complex, in the presence of various factors, including T-cell adhesion molecules (CD54, CD48) and co-stimulatory molecules (CD40, CD80, CD86), induces the maturation of CD4+ T-cells into effector cells (e.g., $T_H1$, $T_H2$, $T_H17$, $T_{FH}$, $T_{reg}$ cells). These effector CD4+ T cells can promote B-cell differentiation to antibody-secreting plasma cells as well as facilitate the differentiation of antigen-specific CD8+ CTLs, thereby helping induce the adaptive immune response to foreign antigens, that include both short-term effector functions and longer-term immunological memory. DCs can perform the process of cross-presentation of peptide antigens by delivering exogenously-derived antigens (such as a peptide or protein released from a pathogen or a tumor cell) onto their MHC I molecules, contributing to the generation of immunological memory by providing an alternative pathway to stimulating the expansion of naïve CD8+ T-cells.

Immunological memory (specifically antigen-specific B cells/antibodies and antigen-specific CTLs) are critical players in controlling microbial infections, and immunological memory has been exploited to develop numerous vaccines that prevent the diseases caused by important pathogenic microbes. Immunological memory is also known to play a key role in controlling tumor formation, but very few efficacious cancer vaccines have been developed.

Cancer is the second leading cause of morbidity, accounting for nearly 1 in 6 of all deaths globally. Of the 8.8 million deaths caused by cancer in 2015, the cancers which claimed the most lives were from lung (1.69 million), liver (788,000), colorectal (774,000), stomach (754,000) and breast (571,000) carcinomas. The economic impact of cancer in 2010 was estimated to be USD1.16 Trillion, and the number of new cases is expected to rise by approximately 70% over the next two decades (World Health Organisation Cancer Facts 2017).

Non small cell lung cancer (NSCLC) represents approximately 80% to 85% of the incidences of lung cancer. Lung squamous cell carcinoma (LUSC) is a subtype of NSCLC and represents approximately 25% to 30% of all lung cancers. LUSC start in early squamous cells of the lung, which are flat cells that line the inside of the airways in the lungs. LUSC generally originates in the bronchi.

Cutaneous melanoma, or melanoma of the skin, is the most common type of melanoma worldwide. Cutaneous melanoma can, for example, be caused by excessive exposure to ultraviolet rays. There are several subtypes of cutaneous melanoma including superficial spreading melanoma, nodular melanoma, lentigo maligna melanoma and amelanotic melanoma.

Current therapies for non small cell lung cancer and cutaneous melanoma are varied and depend highly on the location of the tumor and stage of the disease. One of the main treatments for non small cell lung cancer and cutaneous melanoma is surgery to remove the tumor and surrounding tissue. Later stage non small cell lung cancers and cutaneous melanoma may require treatment comprising lymph node dissection, radiotherapy, or chemotherapy. Immune checkpoint blockade strategies, including the use of antibodies targeting negative immune regulators such PD-1/PD-L1 and CTLA4, have recently revolutionised treatments to a variety of malignancies, including non small cell lung cancer and cutaneous melanoma (Ribas, A., & Wolchok, J. D. (2018) *Science*, 359:1350-1355.). Although these therapies are often highly effective, particularly in melanoma, a significant fraction of cutaneous melanoma patients, and the majority of non small cell lung cancer patients are not cured by the negative immune regulator therapies. Nevertheless, the extraordinary value of checkpoint blockade therapies, and the well-recognized association of their clinical benefit with patient's adaptive immune responses (specifically T cell based immune responses) to their own cancer antigens has re-invigorated the search for effective cancer vaccines, vaccine modalities, and cancer vaccine antigens.

Human endogenous retroviruses (HERVs) are remnants of ancestral germline integrations of exogenous infectious retroviruses. HERVs belong to the group of endogenous retroelements that are characterised by the presence of Long Terminal Repeats (LTRs) flanking the viral genome. This group also includes the Mammalian apparent LTR Retrotransposons (MaLRs) and are therefore collectively known as LTR elements (here referred to collectively as ERV to mean all LTR elements). ERVs constitute a considerable proportion of the mammalian genome (8%), and can be grouped into approximately 100 families based on sequence homology. Many ERV sequences encode defective proviruses which share the prototypical retroviral genomic structure consisting of gag, pro, pol and env genes flanked by LTRs. Some intact ERV ORFs produce retroviral proteins which share features with proteins encoded by exogenous infectious retroviruses such as HIV-1. Such proteins may serve as antigens to induce a potent immune response (Hurst & Magiorkinis, 2015, J. Gen. Virol 96:1207-1218), suggesting that polypeptides encoded by ERVs can escape T and B-cell receptor selection processes and central and peripheral tolerance. Immune reactivity to ERV products may occur spontaneously in infection or cancer, and ERV products have been implicated as a cause of some autoimmune diseases (Kassiotis & Stoye, 2016, Nat. Rev. Immunol. 16:207-219).

Due to the accumulation of mutations and recombination events during evolution, most ERVs have lost functional open reading frames for some or all of their genes and therefore their ability to produce infectious virus. However, these ERV elements are maintained in germline DNA like other genes and still have the potential to produce proteins from at least some of their genes. Indeed, HERV-encoded proteins have been detected in a variety of human cancers. For example, splice variants of the HERV-K env gene, Rec and Np9, are found exclusively in malignant testicular germ cells and not in healthy cells (Ruprecht et. al, 2008, Cell Mol Life Sci 65:3366-3382). Increased levels of HERV transcripts have also been observed in cancers such as those of the prostate, as compared to healthy tissue (Wang-Johanning, 2003, Cancer 98:187-197; Andersson et al., 1998, Int. J. Oncol, 12:309-313). Additionally, overexpression of HERV-E and HERV-H has been demonstrated to be immunosuppressive, which could also contribute to the development of cancer (Mangeney et al., 2001, J. Gen. Virol. 82:2515-2518). However, the exact mechanism(s) by which HERVs could contribute to the development or pathogenicity of cancer remains unknown.

In addition to deregulating the expression of surrounding neighbouring host genes, the activity and transposition of ERV regulatory elements to new genomic sites may lead to the production of novel transcripts, some of which may have oncogenic properties (Babaian & Mager, *Mob. DNA,* 2016, Lock et al., *PNAS,* 2014, 111:3534-3543).

A wide range of vaccine modalities are known. One well-described approach involves directly delivering an antigenic polypeptide to a subject with a view to raising an immune response (including B- and T-cell responses) and stimulating immunological memory. Alternatively, a polynucleotide may be administered to the subject by means of a vector such that the polynuceotide-encoded immunogenic polypeptide is expressed in vivo. The use of viral vectors, for example adenovirus vectors, has been well explored for the delivery of antigens in both prophylactic vaccination and therapeutic treatment strategies against cancer (Wold et al. Current Gene Therapy, 2013, Adenovirus Vectors for Gene Therapy, Vaccination and Cancer Gene Therapy, 13:421-433). Immuogenic peptides, polypeptides, or polynucleotides encoding them, can also be used to load patient-derived antigen presenting cells (APCs), that can then be infused into the subject as a vaccine that elicits a therapeutic or prophylactic immune response. An example of this approach is Provenge, which is presently the only FDA-approved anti-cancer vaccine.

Cancer antigens, may also be exploited in the treatment and prevention of cancer by using them to create a variety of non-vaccine therapeutic modalities. These therapies fall into two different classes: 1) antigen-binding biologics, 2) adoptive cell therapies.

Antigen-binding biologics typically consist of multivalent engineered polypeptides that recognize antigen-decorated cancer cells and facilitate their destruction. The antigen-binding components of these biologics may consist of TCR-based biologicals, including, but not limited to TCRs, high-affinity TCRs, and TCR mimetics produced by various technologies (including those based on monoclonal antibody technologies). Cytolytic moieties of these types of multivalent biologics may consist of cytotoxic chemicals, biological toxins, targeting motifs and/or immune stimulating motifs that facilitate targeting and activation of immune cells, any of which facilitate the therapeutic destruction of tumor cells.

Adoptive cell therapies may be based on a patient's own T cells that are removed and stimulated ex vivo with vaccine antigen preparations (cultivated with T cells in the presence or absence of other factors, including cellular and acellular components) (JCI Insight. 2018 Oct. 4; 3(19). pii: 122467. doi: 10.1172/jci.insight.122467). Alternatively, adoptive cell therapies can be based on cells (including patient- or non-patient-derived cells) that have been deliberately engineered to express antigen-binding polypeptides that recognize cancer antigens. These antigen-binding polypeptides fall into the same classes as those described above for antigen-binding biologics. Thus, lymphocytes (autologous or non-autologous), that have been genetically manipulated to express cancer antigen-binding polypeptides can be administered to a patient as adoptive cell therapies to treat their cancer.

Use of ERV-derived antigens in raising an effective immune response to cancer has shown promising results in promoting tumor regression and a more favourable prognosis in murine models of cancer (Kershaw et al., 2001, Cancer Res. 61:7920-7924; Slansky et al., 2000, Immunity 13:529-538). Thus, HERV antigen-centric immunotherapy trials have been contemplated in humans (Sacha et al., 2012, J. Immunol 189:1467-1479), although progress has been restricted, in part, due to a severe limitation of identified tumor-specific ERV antigens.

WO 2005/099750 identifies anchored sequences in existing vaccines against infectious pathogens, which are common in raising cross-reactive immune responses against the HERV-K Mel tumor antigen and confers protection to melanoma.

WO 00/06598 relates to the identification of HERV-AVL3-B tumor associated genes which are preferentially expressed in melanomas, and methods and products for diagnosing and treating conditions characterised by expression of said genes.

WO 2006/119527 provides antigenic polypeptides derived from the melanoma-associated endogenous retrovirus (MERV), and their use for the detection and diagnosis of melanoma as well as prognosis of the disease. The use of antigenic polypeptides as anticancer vaccines is also disclosed.

WO 2007/137279 discloses methods and compositions for detecting, preventing and treating HERV-K+ cancers, for example with use of a HERV-K+ binding antibody to prevent or inhibit cancer cell proliferation.

WO 2006/103562 discloses a method for treating or preventing cancers in which the immunosuppressive Np9 protein from the env gene of HERV-K is expressed. The invention also relates to pharmaceutical compositions comprising nucleic acid or antibodies capable of inhibiting the activity of said protein, or immunogen or vaccinel composition capable of inducing an immune response directed against said protein.

WO 2007/109583 provides compositions and methods for preventing or treating neoplastic disease in a mammalian subject, by providing a composition comprising an enriched immune cell population reactive to a HERV-E antigen on a tumor cell.

Humer J, et al., 2006, Canc. Res., 66:1658-63 identifies a melanoma marker derived from melanoma-associated endogenous retroviruses.

There is a need to identify further HERV-associated antigenic sequences which can be used in immunotherapy of cancer, particularly non small cell lung cancer, especially lung squamous cell carcinoma, and melanoma, especially cutaneous melanoma.

SUMMARY OF THE INVENTION

The inventors have surprisingly discovered certain RNA transcripts which comprise LTR elements which are found at high levels in non small cell lung cancer specifically lung squamous cell carcinoma, but are undetectable or found at very low levels in normal, healthy tissues (see Example 1). Such transcripts are herein referred to as cancer-specific LTR-element spanning transcripts (CLTs). Further, the inventors have shown that a subset of the potential polypeptide sequences (i.e., open reading frames (ORFs)) encoded by these CLTs are translated in non small cell lung cancer cells, processed by components of the antigen-processing apparatus, and presented on the surface of cells found in tumor tissue in association with class I human leukocyte antigen (HLA class I) molecules (see Example 2). These findings demonstrate that these polypeptides (herein referred to as CLT antigens) are, ipso facto, antigenic. Thus, cancer cell presentation of CLT antigens is expected to render these cells susceptible to elimination by T cells that bear cognate T cell receptors (TCRs) for the CLT antigens, and CLT antigen-based vaccination methods/regimens that amplify T cells bearing these cognate TCRs are expected to elicit immune responses against cancer cells (and tumors containing them), particularly non small cell lung cancer particularly lung squamous cell carcinoma.

The inventors have also surprisingly discovered that a certain CLT antigen-encoding CLT as well as being overexpressed in lung squamous cell carcinoma is also overexpressed in cutaneous melanoma (see Example 1). The potential polypeptide sequence (i.e., open reading frame (ORF)) encoded by this CLT is translated in cutaneous melanoma cancer cells, processed by components of the antigen-processing apparatus, and presented on the surface of cells found in tumor tissue in association with class I human leukocyte antigen (HLA class I) molecules (see Example 2). The CLT antigen polypeptide sequence encoded by this CLT is thus also expected to elicit immune responses against cutaneous melanoma cells and tumors containing them.

The CLTs and the CLT antigens that are the subject of the present invention are not canonical sequences which can be readily derived from known tumor genome sequences found in the cancer genome atlas. The CLTs are transcripts resulting from complex transcription and splicing events driven by transcription control sequences of ERV origin. Since the CLTs are expressed at high level and since CLT antigen polypeptide sequences are not sequences of normal human proteins, it is expected that they will be capable of eliciting strong, specific immune responses and thus suitable for therapeutic use in a cancer immunotherapy setting.

The CLT antigens discovered in the highly expressed transcripts that characterize tumor cells, which prior to the present invention were not known to exist and produce protein products in man, can be used in several formats. First, CLT antigen polypeptides of the invention can be directly delivered to a subject as a vaccine that elicits a therapeutic or prophylactic immune response to tumor cells. Second, nucleic acids of the invention, which may be codon optimised to enhance the expression of their encoded CLT antigens, can be directly administered or else inserted into vectors for delivery in vivo to produce the encoded protein products in a subject as a vaccine that elicits a therapeutic or prophylactic immune response to tumor cells. Third, polynucleotides and/or polypeptides of the invention can be used to load patient-derived antigen presenting cells (APCs), that can then be infused into the subject as a vaccine that elicits a therapeutic or prophylactic immune response to tumor cells. Fourth, polynucleotides and/or polypeptides of the invention can be used for ex vivo stimulation of a subject's T cells, producing a stimulated T cell preparation that can be administered to a subject as a therapy to treat cancer. Fifth, biological molecules such as T cell receptors (TCRs) or TCR mimetics that recognize CLT antigens complexed to MHC I molecules and have been further modified to permit them to kill (or facilitate killing) of cancer cells may be adminsistered to a subject as a therapy to treat cancer. Sixth, chimeric versions of biological molecules that recognize CLT antigens complexed to MHC cells may be introduced into T cells (autologous our non-autologous), and the resulting cells may be administered to a subject as a therapy to treat cancer. These and other applications are described in greater detail below.

Thus, the invention provides inter alia an isolated polypeptide comprising a sequence selected from:

(a) the sequence of any one of SEQ ID NOs. 1-2 and (b) a variant of the sequences of (a); and (c) an immunogenic fragment of the sequences of (a)

(hereinafter referred to as "a polypeptide of the invention").

The invention also provides a nucleic acid molecule which encodes a polypeptide of the invention (hereinafter referred to as "a nucleic acid of the invention").

The polypeptides of the invention and the nucleic acids of the invention, as well as related aspects of the invention, are expected to be useful in a range of embodiments in cancer immunotherapy and prophylaxis, particularly immunotherapy and prophylaxis of non small cell lung cancer and melanoma, as discussed in more detail below.

DESCRIPTION OF THE FIGURES

For each of FIGS. 1-3, the top panel shows an extracted MS/MS spectrum (with assigned fragment ions) of a peptide isolated from a tumor sample of a patient and the bottom panel shows a rendering of the spectrum indicating the positions of the linear peptide sequences that have been mapped to the fragment ions.

Figure 4:
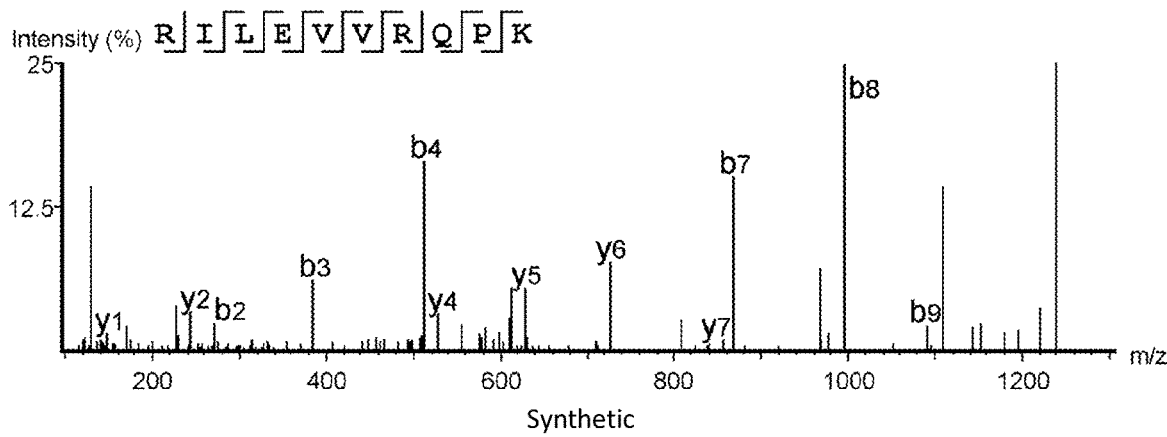
Figure 4:
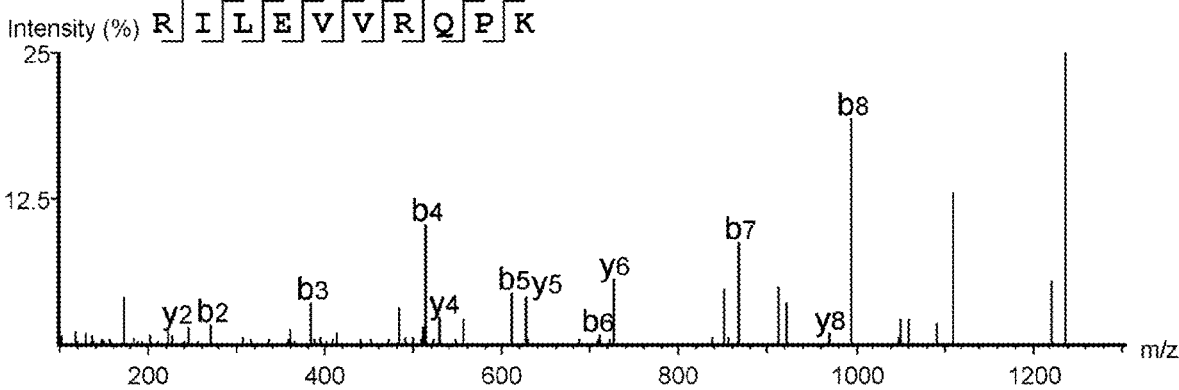
Figure 5:
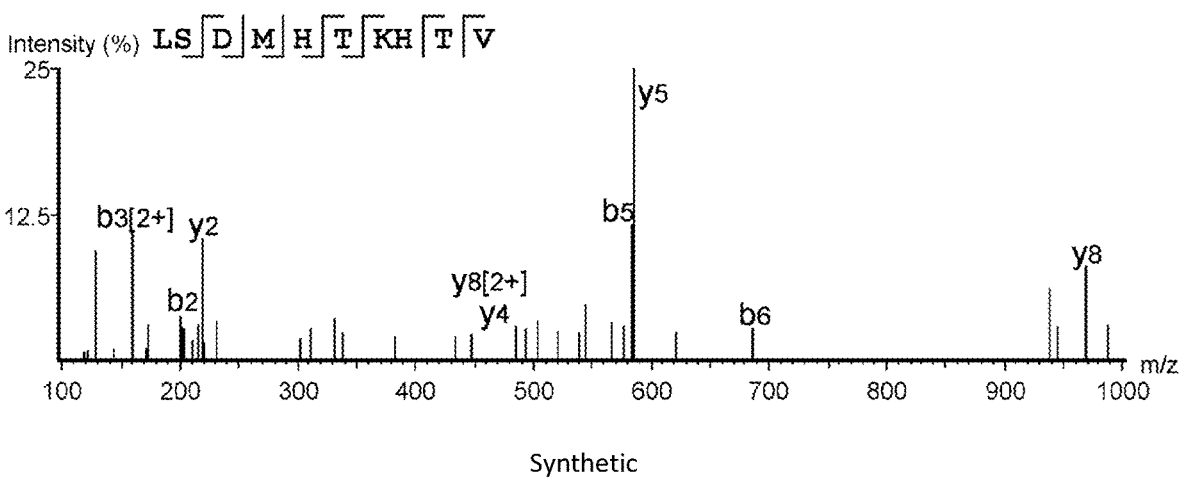
Figure 5:
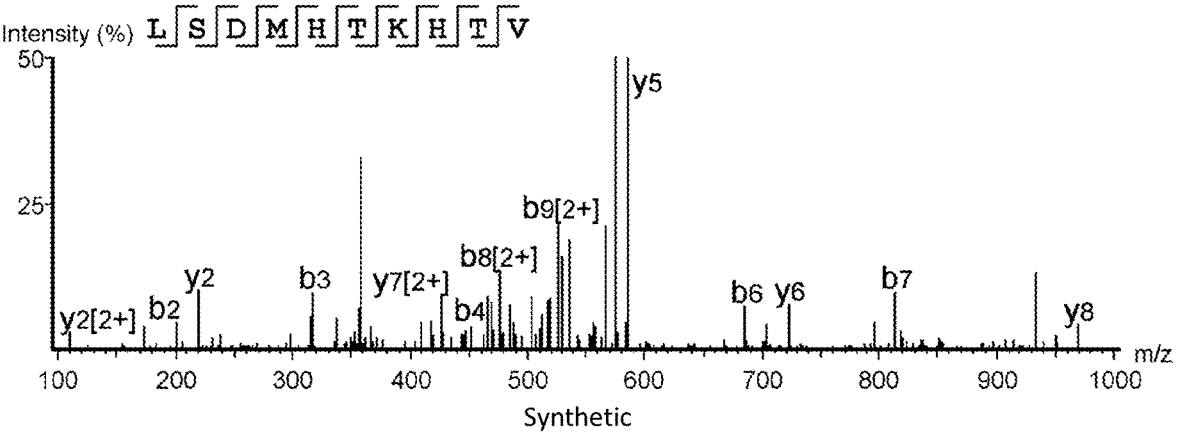
Figure 6:
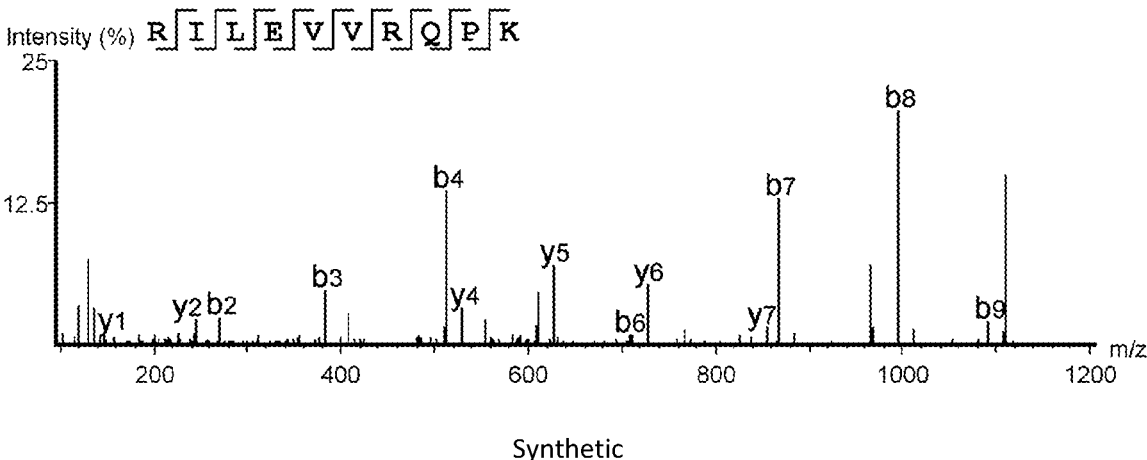
Figure 6:
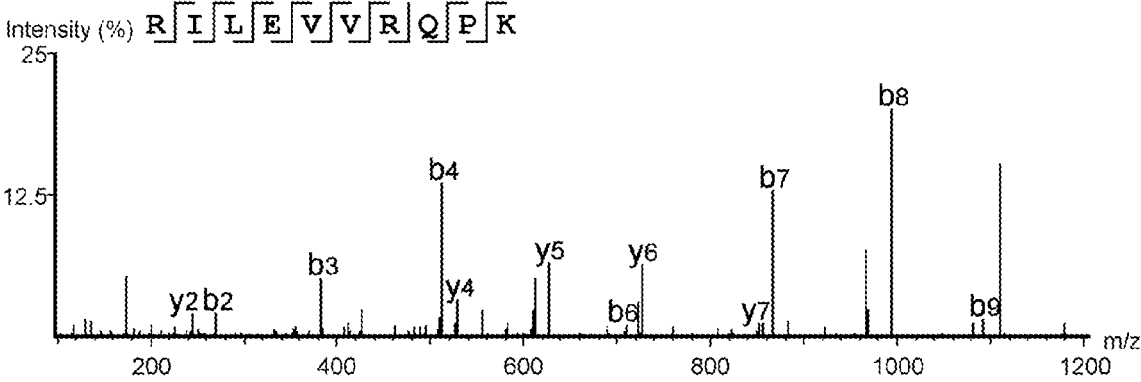

Each of FIGS. 4-6 shows an alignment of a native MS/MS spectrum of a peptide isolated from a patient tumor sample to the native spectrum of a synthetic peptide corresponding to the same sequence.

FIG. 4. Spectra for the peptide of SEQ ID NO. 3 isolated from a lung tumor sample of patient LUSCT8.

FIG. 5. Spectra for the peptide of SEQ ID NO. 4 isolated from a lung tumor sample of patient train_sample_32.

FIG. 6. Spectra for the peptide of SEQ ID NO. 3 isolated from a melanoma tumor sample of patient 2MT3.

Figure 7:
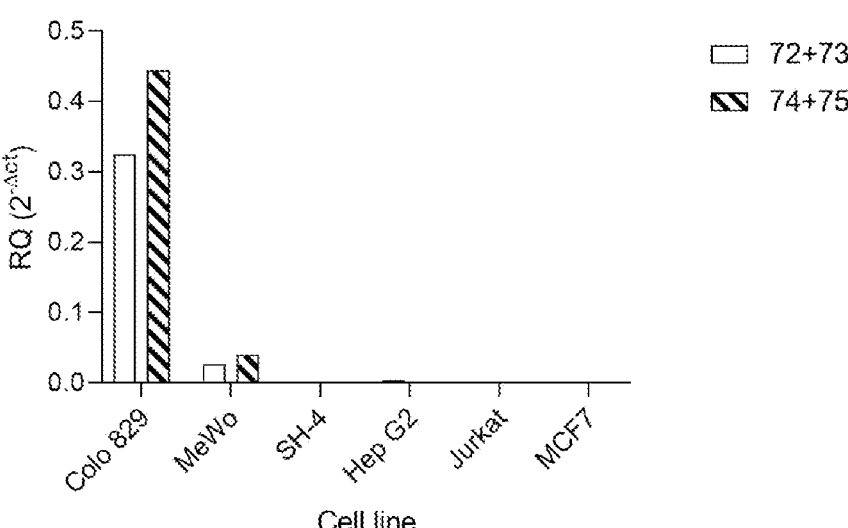

FIG. 7. qRT-PCR assay results to verify the expression of the CLT encoding CLT Antigen 1 (SEQ ID NO. 5) in melanoma cell lines.

DESCRIPTION OF THE SEQUENCES

SEQ ID NO. 1 is the polypeptide sequence of CLT Antigen 1

SEQ ID NO. 2 is the polypeptide sequence of CLT Antigen 2

SEQ ID NO. 3 is a peptide sequence derived from CLT Antigen 1

SEQ ID NO. 4 is a peptide sequence derived from CLT Antigen 2

SEQ ID NO. 5 is the cDNA sequence of the CLT encoding CLT Antigen 1

SEQ ID NO. 6 is the cDNA sequence of the CLT encoding CLT Antigen 2

SEQ ID NO. 7 is a cDNA sequence encoding CLT Antigen 1

SEQ ID NO. 8 is a cDNA sequence encoding CLT Antigen 2

DETAILED DESCRIPTION OF THE INVENTION

Polypeptides

The terms "protein", "polypeptide" and "peptide" are used interchangeably herein and refer to any peptide-linked chain of amino acids, regardless of length, co-translational or post-translational modification.

The term "amino acid" refers to any one of the naturally occurring amino acids, as well as amino acid analogs and amino acid mimetics that function in a manner similar to the naturally occurring amino acids. Naturally occurring amino acids are those 20 L-amino acids encoded by the genetic code, as well as those amino acids that are later modified, e.g., hydroxyproline, γ-carboxyglutamate, and O-phospho-serine. The term "amino acid analogue" refers to a compound that has the same basic chemical structure as a naturally occurring amino acid, i.e., an a carbon that is bound to a hydrogen, a carboxyl group, an amino group, and an R group but has a modified R group or a modified peptide backbone as compared with a natural amino acid. Examples include homoserine, norleucine, methionine sulfoxide, methionine methyl sulfonium and norleucine. Amino acid mimetics refers to chemical compounds that have a structure that is different from the general chemical structure of an amino acid, but that functions in a manner similar to a naturally occurring amino acid. Suitably an amino acid is a naturally occurring amino acid or an amino acid analogue, especially a naturally occurring amino acid and in particular one of those 20 L-amino acids encoded by the genetic code.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Thus, the invention provides an isolated polypeptide comprising a sequence selected from:
(a) the sequence of any one of SEQ ID NOs. 1-2; and
(b) a variant of the sequences of (a); and
(c) an immunogenic fragment of the sequences of (a)

The invention also provides an isolated polypeptide comprising a sequence selected from:
(a) the sequence of any one of SEQ ID NOs. 1-2 minus the initial methionine residue; and
(b) a variant of the sequences of (a); and
(c) an immunogenic fragment of the sequences of (a)

In general, variants of polypeptide sequences of the invention include sequences having a high degree of sequence identity thereto. For example variants suitably have at least about 80% identity, more preferably at least about 85% identity and most preferably at least about 90% identity (such as at least about 95%, at least about 98% or at least about 99%) to the associated reference sequence over their whole length.

Suitably the variant is an immunogenic variant. A variant is considered to be an immunogenic variant where it elicits a response which is at least 20%, suitably at least 50% and especially at least 75% (such as at least 90%) of the activity of the reference sequence (i.e. the sequence of which the variant is a variant) e.g., in an in vitro restimulation assay of PBMC or whole blood with the polypeptide as antigen (e.g., restimulation for a period of between several hours to up to 1 year, such as up to 6 months, 1 day to 1 month or 1 to 2 weeks), that measures the activation of the cells via lymphoproliferation (e.g., T-cell proliferation), production of cytokines (e.g., IFN-gamma) in the supernatant of culture (measured by ELISA etc.) or characterisation of T cell responses by intra and extracellular staining (e.g., using antibodies specific to immune markers, such as CD3, CD4, CD8, IL2, TNF-alpha, IFNg, Type 1 IFN, CD40L, CD69 etc.) followed by analysis with a flow cytometer.

The variant may, for example, be a conservatively modified variant. A "conservatively modified variant" is one where the alteration(s) results in the substitution of an amino acid with a functionally similar amino acid or the substitution/deletion/addition of residues which do not substantially impact the biological function of the variant. Typically, such biological function of the variants will be to induce an immune response against a non small cell lung cancer e.g. a lung squamous cell carcinoma antigen or a melanoma e.g. cutaneous melanoma cancer antigen.

Conservative substitution tables providing functionally similar amino acids are well known in the art. Variants can include homologues of polypeptides found in other species.

A variant of a polypeptide of the invention may contain a number of substitutions, for example, conservative substitutions (for example, 1-25, such as 1-10, in particular 1-5, and especially 1 amino acid residue(s) may be altered) when compared to the reference sequence. The number of substitutions, for example, conservative substitutions, may be up to 20% e.g., up to 10% e.g., up to 5% e.g., up to 1% of the number of residues of the reference sequence. In general, conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:
1) Alanine (A), Glycine (G);
2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M) (see, e.g., Creighton, Proteins 1984).

Suitably such substitutions do not alter the immunological structure of an epitope (e.g., they do not occur within the epitope region as mapped in the primary sequence), and do not therefore have a significant impact on the immunogenic properties of the antigen.

Polypeptide variants also include those wherein additional amino acids are inserted compared to the reference sequence, for example, such insertions may occur at 1-10 locations (such as 1-5 locations, suitably 1 or 2 locations, in particular 1 location) and may, for example, involve the addition of 50 or fewer amino acids at each location (such as 20 or fewer, in particular 10 or fewer, especially 5 or fewer). Suitably such insertions do not occur in the region of an epitope, and do not therefore have a significant impact on the immunogenic properties of the antigen. One example of insertions includes a short stretch of histidine residues (e.g., 2-6 residues) to aid expression and/or purification of the antigen in question.

Polypeptide variants include those wherein amino acids have been deleted compared to the reference sequence, for example, such deletions may occur at 1-10 locations (such as 1-5 locations, suitably 1 or 2 locations, in particular 1 location) and may, for example, involve the deletion of 50 or fewer amino acids at each location (such as 20 or fewer, in particular 10 or fewer, especially 5 or fewer). Suitably such deletions do not occur in the region of an epitope, and do not therefore have a significant impact on the immunogenic properties of the antigen.

The skilled person will recognise that a particular protein variant may comprise substitutions, deletions and additions (or any combination thereof). For example, substitutions/deletions/additions might enhance (or have neutral effects) on binding to desired patient HLA molecules, potentially increasing immunogenicity (or leaving immunogenicity unchanged).

Immunogenic fragments according to the present invention will typically comprise at least 9 contiguous amino acids from the full-length polypeptide sequence (e.g., at least 9 or 10), such as at least 12 contiguous amino acids (e.g., at least 15 or at least 20 contiguous amino acids), in particular at least 50 contiguous amino acids, such as at least 100 contiguous amino acids (for example at least 200 contiguous amino acids) depending on the length of the CLT antigen. Suitably the immunogenic fragments will be at least 20%, such as at least 50%, at least 70% or at least 80% of the length of the full-length polypeptide sequence.

Immunogenic fragments typically comprise at least one epitope. Epitopes include B cell and T cell epitopes and suitably immunogenic fragments comprise at least one T-cell epitope such as a CD4+ or a CD8+ T-cell epitope.

T cell epitopes are short contiguous stretches of amino acids which are recognised by T cells (e.g., CD4+ or CD8+ T cells) when bound to HLA molecules. Identification of T cell epitopes may be achieved through epitope mapping experiments which are well known to the person skilled in the art (see, for example, Paul, *Fundamental Immunology*, 3rd ed., 243-247 (1993); Beiβbarth et al., 2005, *Bioinformatics*, 21(Suppl. 1):i29-i37).

As a result of the crucial involvement of the T cell response in cancer, it is readily apparent that fragments of the full-length polypeptides of SEQ ID NOs. 1-2 which contain at least one T cell epitope may be immunogenic and may contribute to immunoprotection.

It will be understood that in a diverse outbred population, such as humans, different HLA types mean that specific epitopes may not be recognised by all members of the population. Consequently, to maximise the level of recognition and scale of immune response to a polypeptide, it is generally desirable that an immunogenic fragment contains a plurality of the epitopes from the full-length sequence (suitably all epitopes within a CLT antigen).

Particular fragments of the polypeptides of SEQ ID NOs. 1-2 which may be of use include those containing at least one CD8+ T-cell epitope, suitably at least two CD8+ T-cell epitopes and especially all CD8+ T-cell epitopes, particularly those associated with a plurality of HLA alleles, e.g., those associated with 2, 3, 4, 5 or more alleles). Particular fragments of the polypeptides of SEQ ID NOs. 1-2 which may be of use include those containing at least one CD4+ T-cell epitope, suitably at least two CD4+ T-cell epitopes and especially all CD4+ T-cell epitopes (particularly those associated with a plurality of HLA alleles, e.g., those associated with 2, 3, 4, 5 or more alleles). However, a person skilled in design of vaccines could combine exogenous CD4+ T-cell epitopes with CD8+ T cells epitopes of this invention and achieve desired responses to the invention's CD8+ T cell epitopes.

Where an individual fragment of the full-length polypeptide is used, such a fragment is considered to be immunogenic where it elicits a response which is at least 20%, suitably at least 50% and especially at least 75% (such as at least 90%) of the activity of the reference sequence (i.e., the sequence of which the fragment is a fragment) e.g., activity in an in vitro restimulation assay of PBMC or whole blood with the polypeptide as antigen (e.g., restimulation for a period of between several hours to up to 1 year, such as up to 6 months, 1 day to 1 month or 1 to 2 weeks,) that measures the activation of the cells via lymphoproliferation (e.g., T-cell proliferation), production of cytokines (e.g., IFN-gamma) in the supernatant of culture (measured by ELISA etc.) or characterisation of T cell responses by intra and extracellular staining (e.g., using antibodies specific to immune markers, such as CD3, CD4, CD8, IL2, TNF-alpha, IFN-gamma, Type 1 IFN, CD40L, CD69 etc.) followed by analysis with a flow cytometer.

In some circumstances a plurality of fragments of the full-length polypeptide (which may or may not be overlapping and may or may not cover the entirety of the full-length sequence) may be used to obtain an equivalent biological response to the full-length sequence itself. For example, at least two immunogenic fragments (such as three, four or five) as described above, which in combination provide at least 50%, suitably at least 75% and especially at least 90% activity of the reference sequence in an in vitro restimulation assay of PBMC or whole blood (e.g., a T cell proliferation and/or IFN-gamma production assay).

Example immunogenic fragments of polypeptides of SEQ ID NOs. 1-2, and thus example peptides of the invention, include polypeptides which comprise or consist of the sequences of SEQ ID NOs. 3-4. The sequences of SEQ ID NOs. 3-4 were identified as being HLA bound from immunopeptidomic analysis (see Example 2).

Nucleic Acids

The invention provides an isolated nucleic acid encoding a polypeptide of the invention (referred to as a nucleic acid of the invention). For example, the nucleic acid of the invention comprises or consists of a sequence selected from SEQ ID NOs. 5-6 or 7-8.

The terms "nucleic acid" and "polynucleotide" are used interchangeably herein and refer to a polymeric macromolecule made from nucleotide monomers particularly deoxyribonucleotide or ribonucleotide monomers. The term encompasses nucleic acids containing known nucleotide analogs or modified backbone residues or linkages, which are naturally occurring and non-naturally occurring, which have similar properties as the reference nucleic acid, and which are intended to be metabolized in a manner similar to the reference nucleotides or are intended to have extended half-life in the system. Examples of such analogs include, without limitation, phosphorothioates, phosphoramidates, methyl phosphonates, chiral-methyl phosphonates, 2-O-methyl ribonucleotides, peptide-nucleic acids (PNAs). Suitably the term "nucleic acid" refers to naturally occurring polymers of deoxyribonucleotide or ribonucleotide monomers. Suitably the nucleic acid molecules of the invention are recombinant. Recombinant means that the nucleic acid molecule is the product of at least one of cloning, restriction or ligation steps, or other procedures that result in a nucleic acid molecule that is distinct from a nucleic acid molecule found in nature (e.g., in the case of cDNA). In an embodiment the nucleic acid of the invention is an artificial nucleic acid sequence (e.g., a cDNA sequence or nucleic acid sequence with non-naturally occurring codon usage). In one embodiment, the nucleic acids of the invention are DNA. Alternatively, the nucleic acids of the invention are RNA.

DNA (deoxyribonucleic acid) and RNA (ribounucleic acid) refer to nucleic acid molecules having a backbone of sugar moieties which are deoxyribosyl and ribosyl moieties respectively. The sugar moieties may be linked to bases which are the 4 natural bases (adenine (A), guanine (G), cytosine (C) and thymine (T) in DNA and adenine (A), guanine (G), cytosine (C) and uracil (U) in RNA). As used herein, a "corresponding RNA" is an RNA having the same sequence as a reference DNA but for the substitution of thymine (T) in the DNA with uracil (U) in the RNA. The sugar moieties may also be linked to unnatural bases such as inosine, xanthosine, 7-methylguanosine, dihydrouridine and 5-methylcytidine. Natural phosphodiester linkages between sugar (deoxyribosyl/ribosyl) moieties may optionally be replaced with phosphorothioates linkages. Suitably nucleic acids of the invention consist of the natural bases attached to a deoxyribosyl or ribosyl sugar backbone with phosphodiester linkages between the sugar moieties.

In an embodiment the nucleic acid of the invention is a DNA. For example the nucleic acid comprises or consists of a sequence selected from SEQ ID NOs. 5-6 or 7-8. Also provided is a nucleic acid which comprises or consists of a variant of sequence selected from SEQ ID NOs. 5-6 or 7-8 which variant encodes the same amino acid sequence but has a different nucleic acid based on the degeneracy of the genetic code.

Thus, due to the degeneracy of the genetic code, a large number of different, but functionally identical nucleic acids can encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations lead to "silent" (sometimes referred to as "degenerate" or "synonymous") variants, which are one species of conservatively modified variations. Every nucleic acid sequence disclosed herein which encodes a polypeptide also enables every possible silent variation of the nucleic acid. One of skill will recognise that each codon in a nucleic acid (except AUG, which is ordinarily the only codon for methionine, and UGG, which is ordinarily the only codon for tryptophan) can be modified to yield a functionally identical molecule. Accordingly, each silent variation of a nucleic acid that encodes a polypeptide is implicit in each described sequence and is provided as an aspect of the invention.

Degenerate codon substitutions may also be achieved by generating sequences in which the third position of one or more selected (or all) codons is substituted with mixed-base and/or deoxyinosine residues (Batzer et al., 1991, Nucleic Acid Res. 19:5081; Ohtsuka et al., 1985, J. Biol. Chem. 260:2605-2608; Rossolini et al., 1994, Mol. Cell. Probes 8:91-98).

A nucleic acid of the invention which comprises or consists of a sequence selected from SEQ ID NOs. 5-6 or 7-8 may contain a number of silent variations (for example, 1-50, such as 1-25, in particular 1-5, and especially 1 codon(s) may be altered) when compared to the reference sequence.

In an embodiment the nucleic acid of the invention is an RNA. RNA sequences are provided which correspond to a DNA sequence provided herein and have a ribonucleotide backbone instead of a deoxyribonucleotide backbone and have the sidechain base uracil (U) in place of thymine (T).

Thus a nucleic acid of the invention comprises or consists of the RNA equivalent of a cDNA sequence selected from SEQ ID NOs. 5-6 or 7-8 and may contain a number of silent variations (for example, 1-50, such as 1-25, in particular 1-5, and especially 1 codon(s) may be altered) when compared to the reference sequence. By "RNA equivalent" is meant an RNA sequence which contains the same genetic information as the reference cDNA sequence (i.e. contains the same codons with a ribonucleotide backbone instead of a deoxyribonucleotide backbone and having the sidechain base uracil (U) in place of thymine (T)).

The invention also comprises sequences which are complementary to the aforementioned cDNA and RNA sequences.

In an embodiment, the nucleic acids of the invention are codon optimised for expression in a human host cell.

The nucleic acids of the invention are capable of being transcribed and translated into polypeptides of the invention in the case of DNA nucleic acids, and translated into polypeptides of the invention in the case of RNA nucleic acids.

Polypeptides and Nucleic Acids

Suitably, the polypeptides and nucleic acids used in the present invention are isolated. An "isolated" polypeptide or nucleic acid is one that is removed from its original environment. For example, a naturally-occurring polypeptide or nucleic acid is isolated if it is separated from some or all of the coexisting materials in the natural system. A nucleic acid is considered to be isolated if, for example, it is cloned into a vector that is not a part of its natural environment.

"Naturally occurring" when used with reference to a polypeptide or nucleic acid sequence means a sequence found in nature and not synthetically modified.

"Artificial" when used with reference to a polypeptide or nucleic acid sequence means a sequence not found in nature which is, for example, a synthetic modification of a natural sequence, or contains an unnatural sequence.

The term "heterologous" when used with reference to the relationship of one nucleic acid or polypeptide to another nucleic acid or polypeptide indicates that the two or more sequences are not found in the same relationship to each other in nature. A "heterologous" sequence can also mean a sequence which is not isolated from, derived from, or based upon a naturally occurring nucleic acid or polypeptide sequence found in the host organism.

As noted above, polypeptide variants preferably have at least about 80% identity, more preferably at least about 85% identity and most preferably at least about 90% identity (such as at least about 95%, at least about 98% or at least about 99%) to the associated reference sequence over their whole length.

For the purposes of comparing two closely-related polypeptide or polynucleotide sequences, the "% sequence identity" between a first sequence and a second sequence may be calculated. Polypeptide sequences are said to be the same as or identical to other polypeptide sequences, if they share 100% sequence identity over their entire length. Residues in sequences are numbered from left to right, i.e. from N- to C-terminus for polypeptides. The terms "identical" or percentage "identity", in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window. Suitably, the comparison is performed over a window corresponding to the entire length of the reference sequence.

For sequence comparison, one sequence acts as the reference sequence, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerised implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, 1987, *J. Mol. Evol.* 35:351-360. The method used is similar to the method described by Higgins & Sharp, 1989, *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984, *Nuc. Acids Res.* 12:387-395).

Another example of algorithm that is suitable for determining percent sequence identity and sequence similarity are the BLAST and BLAST 2.0 algorithms, which are described in Altschul et al., 1977, *Nuc. Acids Res.* 25:3389-3402 and Altschul et al., 1990, *J. Mol. Biol.* 215:403-410, respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For amino acid sequences, the BLASTP program uses as defaults a wordlength of 3, and expectation (E) of 10, and the BLOSUM62 scoring matrix (see Henikoff & Henikoff, 1989, *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance.

A "difference" between sequences refers to an insertion, deletion or substitution of a single residue in a position of the second sequence, compared to the first sequence. Two sequences can contain one, two or more such differences. Insertions, deletions or substitutions in a second sequence which is otherwise identical (100% sequence identity) to a first sequence result in reduced % sequence identity. For example, if the identical sequences are 9 residues long, one substitution in the second sequence results in a sequence identity of 88.9%. If the identical sequences are 17 amino acid residues long, two substitutions in the second sequence results in a sequence identity of 88.2%.

Alternatively, for the purposes of comparing a first, reference sequence to a second, comparison sequence, the number of additions, substitutions and/or deletions made to the first sequence to produce the second sequence may be ascertained. An addition is the addition of one residue into the first sequence (including addition at either terminus of the first sequence). A substitution is the substitution of one residue in the first sequence with one different residue. A deletion is the deletion of one residue from the first sequence (including deletion at either terminus of the first sequence).

Production of Polypeptides of the Invention

Polypeptides of the invention can be obtained and manipulated using the techniques disclosed for example in Green and Sambrook 2012 Molecular Cloning: A Laboratory Manual 4th Edition Cold Spring Harbour Laboratory Press. In particular, artificial gene synthesis may be used to produce polynucleotides (Nambiar et al., 1984, *Science,* 223:1299-1301, Sakamar and Khorana, 1988, *Nucl. Acids Res.,* 14:6361-6372, Wells et al., 1985, *Gene,* 34:315-323 and Grundstrom et al., 1985, *Nucl. Acids Res.,* 13:3305-3316) followed by expression in a suitable organism to produce polypeptides. A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma and Eckstein, 1998, *Annu. Rev. Biochem.* 67:99-134). These relatively short segments are readily assembled by using a variety of gene amplification methods (Methods Mol Biol., 2012; 834:93-109) into longer DNA molecules, suitable for use in innumerable recombinant DNA-based expression systems. In the context of this invention one skilled in the art would understand that the polynucleotide sequences encoding the polypeptide antigens described in this invention could be readily used in a variety of vaccine production systems, including, for example, viral vectors.

For the purposes of production of polypeptides of the invention in a microbiological host (e.g., bacterial or fungal), nucleic acids of the invention will comprise suitable regulatory and control sequences (including promoters, termination signals etc) and sequences to promote polypeptide secretion suitable for protein production in the host. Similarly, polypeptides of the invention could be produced by transducing cultures of eukaryotic cells (e.g., Chinese hamster ovary cells or drosophila S2 cells) with nucleic acids of the invention which have been combined with suitable regulatory and control sequences (including promoters, termination signals etc) and sequences to promote polypeptide secretion suitable for protein production in these cells.

Improved isolation of the polypeptides of the invention produced by recombinant means may optionally be facilitated through the addition of a stretch of histidine residues (commonly known as a His-tag) towards one end of the polypeptide.

Polypeptides may also be produced synthetically.

Vectors

In additional embodiments, genetic constructs comprising one or more of the nucleic acids of the invention are introduced into cells in vivo such that a polypeptide of the invention is produced in vivo eliciting an immune response. The nucleic acid (e.g., DNA) may be present within any of a variety of delivery systems known to those of ordinary skill in the art, including nucleic acid expression systems, bacteria and some viral expression systems. Numerous gene delivery techniques are well known in the art, such as those described by Rolland, 1998, Crit. Rev. Therap. Drug Carrier Systems 15:143-198, and references cited therein. Several of these approaches are outlined below for the purpose of illustration.

Accordingly, there is provided a vector (also referred to herein as a 'DNA expression construct' or 'construct') comprising a nucleic acid molecule of the invention.

Suitably, the vector comprises nucleic acid encoding regulatory elements (such as a suitable promoter and terminating signal) suitable for permitting transcription of a translationally active RNA molecule in a human host cell. A "translationally active RNA molecule" is an RNA molecule capable of being translated into a protein by a human cell's translation apparatus.

Accordingly, there is provided a vector comprising a nucleic acid of the invention (herein after a "vector of the invention").

In particular, the vector may be a viral vector. The viral vector may be an adenovirus, adeno-associated virus (AAV) (e.g., AAV type 5 and type 2), alphavirus (e.g., Venezuelan equine encephalitis virus (VEEV), Sindbis virus (SIN), Semliki Forest virus (SFV), herpes virus, arenavirus (e.g., lymphocytic choriomeningitis virus (LCMV)), measles virus, poxvirus (such as modified vaccinia Ankara (MVA)), paramyxovirus, lentivirus, or rhabdovirus (such as vesicular stomatitis virus (VSV)) vector i.e. the vector may be derived from any of the aforementioned viruses. Adenoviruses are particularly suitable for use as a gene transfer vector because of its mid-sized genome, ease of manipulation, high titre, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP is particularly efficient during the late phase of infection, and all the mRNAs trasncribed from this promoter possess a 5'-tripartite leader (TPL) sequence which makes them preferred mRNAs for translation. Replication-deficient adenovirus, which are created by from viral genomes that are deleted for one or more of the early genes are particularly useful, since they have limited replication and less possibility of pathogenic spread within a vaccinated host and to contacts of the vaccinated host.

Other Polynucleotide Delivery

In certain embodiments of the invention, the expression construct comprising one or more polynucleotide sequences may simply consist of naked recombinant DNA plasmids. See Ulmer et al., 1993, *Science* 259:1745-1749 and reviewed by Cohen, 1993, *Science* 259:1691-1692. Transfer of the construct may be performed, for example, by any method which physically or chemically permeabilises the cell membrane. This is particularly applicable for transfer in vitro but it may be applied to in vivo use as well. It is envisioned that DNA encoding a gene of interest may also be transferred in a similar manner in vivo and express the gene product. Multiple delivery systems have been used to deliver DNA molecules into animal models and into man. Some products based on this technology have been licensed for use in animals, and others are in phase 2 and 3 clinical trials in man.

RNA Delivery

In other embodiments of the invention, the expression construct comprising one or more polynucleotide sequences may consist of naked, recombinant DNA-derived RNA molecules (Ulmer et al., 2012, Vaccine 30:4414-4418). As for DNA-based expression constructs, a variety of methods can be utilized to introduce RNA molecules into cells in vitro or in vivo. The RNA-based constructs can be designed to mimic simple messenger RNA (mRNA) molecules, such that the introduced biological molecule is directly translated by the host cell's translation machinery to produce its encoded polypeptide in the cells to which it has been introduced. Alternatively, RNA molecules may be designed in a manner that allows them to self-amplify within cells they are introduced into, by incorporating into their structure genes for viral RNA-dependent RNA polymerases. Thus, these types of RNA molecules, known as self-amplifying mRNA (SAM™) molecules (Geall et al. 2012, PNAS, 109:14604-14609), share properties with some RNA-based viral vectors. Either mRNA-based or SAM™ RNAs may be further modified (e.g., by alteration of their sequences, or by use of modified nucleotides) to enhance stability and translation (Schlake et al., RNA Biology, 9: 1319-1330), and both types of RNAs may be formulated (e.g., in emulsions (Brito et al., Molecular Therapy, 2014 22:2118-2129) or lipid nanoparticles (Kranz et al., 2006, *Nature*, 534:396-401)) to facilitate stability and/or entry into cells in vitro or in vivo. Myriad formulations of modified (and non-modified) RNAs have been tested as vaccines in animal models and in man, and multiple RNA-based vaccines are being used in ongoing clinical trials.

Pharmaceutical Compositions

The polypeptides, nucleic acids and vectors of the invention may be formulated for delivery in pharmaceutical compositions such as immunogenic compositions and vaccine compositions (all hereinafter "compositions of the invention"). Compositions of the invention suitably comprise a polypeptide, nucleic acid or vector of the invention together with a pharmaceutically acceptable carrier.

Thus, in an embodiment, there is provided an immunogenic pharmaceutical composition comprising a polypeptide, nucleic acid or vector of the invention together with a pharmaceutically acceptable carrier.

In another embodiment there is provided a vaccine composition comprising a polypeptide, nucleic acid or vector of the invention together with a pharmaceutically acceptable carrier. Preparation of pharmaceutical compositions is generally described in, for example, Powell & Newman, eds., *Vaccine Design* (the subunit and adjuvant approach), 1995. Compositions of the invention may also contain other compounds, which may be biologically active or inactive. Suitably, the composition of the invention is a sterile composition suitable for parenteral administration.

In certain preferred embodiments of the present invention, pharmaceutical compositions of the invention are provided which comprise one or more (e.g., one) polypeptides of the invention in combination with a pharmaceutically acceptable carrier.

In certain preferred embodiments of the present invention, compositions of the invention are provided which comprise one or more (e.g., one) nucleic acids of the invention or one or more (e.g., one) vectors of the invention in combination with a pharmaceutically acceptable carrier.

In an embodiment, the compositions of the invention may comprise one or more (e.g., one) polynucleotide and one or more (e.g., one) polypeptide components. Alternatively, the compositions may comprise one or more (e.g., one) vector and one or more (e.g., one) polypeptide components. Alternatively, the compositions may comprise one or more (e.g., one) vector and one or more (e.g., one) polynucleotide components. Such compositions may provide for an enhanced immune response.

Pharmaceutically Acceptable Salts

It will be apparent that a composition of the invention may contain pharmaceutically acceptable salts of the nucleic acids or polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

Pharmaceutically Acceptable Carriers

While many pharmaceutically acceptable carriers known to those of ordinary skill in the art may be employed in the compositions of the invention, the optimal type of carrier used will vary depending on the mode of administration. Compositions of the present invention may be formulated for any appropriate manner of administration, including for example, parenteral, topical, oral, nasal, intravenous, intracranial, intraperitoneal, subcutaneous or intramuscular administration, preferably parenteral e.g., intramuscular, subcutaneous or intravenous administration. For parenteral administration, the carrier preferably comprises water and may contain buffers for pH control, stabilising agents e.g., surfactants and amino acids and tonicity modifying agents e.g., salts and sugars. If the composition is intended to be provided in lyophilised form for dilution at the point of use, the formulation may contain a lyoprotectant e.g., sugars such as trehalose. For oral administration, any of the above carriers or a solid carrier, such as mannitol, lactose, starch, magnesium stearate, sodium saccharine, talcum, cellulose, glucose, sucrose, and magnesium carbonate, may be employed.

Thus, compositions of the invention may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, solutes that render the formulation isotonic, hypotonic or weakly hypertonic with the blood of a recipient, suspending agents, thickening agents and/or preservatives. Alternatively, compositions of the invention may be formulated as a lyophilizate.

Immunostimulants Compositions of the invention may also comprise one or more immunostimulants. An immunostimulant may be any substance that enhances or potentiates an immune response (antibody and/or cell-mediated) to an exogenous antigen. Examples of immunostimulants, which are often referred to as adjuvants in the context of vaccine formulations, include aluminium salts such as aluminium hydroxide gel (alum) or aluminium phosphate, saponins including QS21, immunostimulatory oligonucleotides such as CPG, oil-in-water emulsion (e.g., where the oil is squalene), aminoalkyl glucosaminide 4-phosphates, lipopolysaccharide or a derivative thereof e.g., 3-de-O-acylated monophosphoryl lipid A (3D-MPLO®) and other TLR4 ligands, TLR7 ligands, TLR8 ligands, TLR9 ligands, IL-12 and interferons. Thus, suitably the one or more immunostimulants of the composition of the invention are selected from aluminium salts, saponins, immunostimulatory oligonucleotides, oil-in-water emulsions, aminoalkyl glucosaminide 4-phosphates, lipopolysaccharides and derivatives thereof and other TLR4 ligands, TLR7 ligands, TLR8 ligands and TLR9 ligands.

In the case of recombinant-nucleic acid methods of delivery (e.g., DNA, RNA, viral vectors), the genes encoding protein-based immunostimulants may be readily delivered along with the genes encoding the polypeptides of the invention.

Sustained Release

The compositions described herein may be administered as part of a sustained-release formulation (i.e., a formulation such as a capsule, sponge, patch or gel (composed of polysaccharides, for example)) that effects a slow/sustained release of compound following administration.

Storage and Packaging

Compositions of the invention may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a composition of the invention may be stored in a freeze-dried condition requiring only the addition of a sterile liquid carrier (such as water or saline for injection) immediately prior to use.

Dosage

The amount of nucleic acid, polypeptide or vector in each composition of the invention may be prepared is such a way that a suitable dosage for therapeutic or prophylactic use will be obtained. Factors such as solubility, bioavailability, biological half-life, route of administration, product shelf life, as well as other pharmacological considerations will be contemplated by one skilled in the art of preparing such compositions, and as such, a variety of dosages and treatment regimens may be desirable.

Typically, compositions comprising a therapeutically or prophylactically effective amount deliver about 0.1 ug to about 1000 ug of polypeptide of the invention per administration, more typically about 2.5 ug to about 100 ug of polypeptide per administration. If delivered in the form of short, synthetic long peptides, doses could range from 1 to 200 ug/peptide/dose. In respect of polynucleotide compositions, these typically deliver about 10 ug to about 20 mg of the nucleic acid of the invention per administration, more typically about 0.1 mg to about 10 mg of the nucleic acid of the invention per administration.

Diseases to be Treated or Prevented

As noted elsewhere, SEQ ID NO. 1 is a polypeptide sequence corresponding to CLT Antigen 1 which is over-expressed in lung squamous cell carcinoma and cutaneous melanoma. SEQ ID NO. 2 is a polypeptide sequence corresponding to CLT Antigen 2 which is over-expressed in lung squamous cell carcinoma.

In one embodiment, the invention provides a polypeptide, nucleic acid, vector or composition of the invention for use in medicine.

Further aspects of the invention relate to a method of raising an immune response in a human which comprises administering to said human the polypeptide, nucleic acid, vector or composition of the invention.

The present invention also provides a polypeptide, nucleic acid, vector or composition of the invention for use in raising an immune response in a human.

There is also provided a use of a polypeptide, nucleic acid, vector or composition of the invention for the manufacture of a medicament for use in raising an immune response in a human.

Suitably the immune response is raised against a cancerous tumor expressing a corresponding sequence selected from SEQ ID NOs. 1-2 and variants and immunogenic fragments of any one thereof. By "corresponding" in this context is meant that if the tumor expresses, say, SEQ ID NO. A (A being one of SEQ ID NOs. 1-2) or a variant or immunogenic fragment thereof then the polypeptide, nucleic acid, vector or composition of the invention and medicaments involving these will be based on SEQ ID NO. A or a variant or immunogenic fragment thereof.

Suitably the immune response comprises CD8+ T-cell, a CD4+ T-cell and/or an antibody response, particularly CD8+ cytolytic T-cell response and a CD4+ helper T-cell response.

Suitably the immune response is raised against a tumor, particularly one expressing a sequence selected from SEQ ID NOs. 1-2 and variants thereof and immunogenic fragments thereof.

In a preferred embodiment, the tumor is a non small cell lung tumor e.g. a lung squamous cell carcinoma tumor.

The tumor may be a primary tumor or a metastatic tumor.

Further aspects of the invention relate to a method of treating a human patient suffering from cancer wherein the cells of the cancer express a sequence selected from SEQ ID NOs. 1-2 and immunogenic fragments and variants of any one thereof, or of preventing a human from suffering from cancer which cancer would express a sequence selected from SEQ ID NOs. 1-2 and immunogenic fragments and variants of any one thereof, which method comprises administering to said human a corresponding polypeptide, nucleic acid, vector or composition of the invention.

The present invention also provides a polypeptide, nucleic acid, vector or composition of the invention for use in treating or preventing cancer in a human, wherein the cells of the cancer express a corresponding sequence selected from SEQ ID NOs. 1-2 and immunogenic fragments of any one thereof.

A transcript corresponding to SEQ ID NO. 5 was also overexpressed in cutaneous melanoma. Consequently, in an alternative embodiment, the tumor is melanoma tumor particularly a cutaneous melanoma tumor and/or the tumor expresses a sequence selected from SEQ ID NO. 1 and immunogenic fragments thereof.

Thus, the invention provides a method or a polypeptide, nucleic acid, vector or composition for use according to the invention wherein the polypeptide comprises a sequence selected from:

(a) the sequence of SEQ ID NO. 1; and (b) a variant of the sequences of (a); and (c) an immunogenic fragment of the sequences of (a).

and for example the polypeptide comprises or consists of SEQ ID NO. 3 and for example the nucleic acid comprises or consists of a sequence selected from any one of SEQ ID NOs. 5 or 7;

and wherein the cancer is melanoma, particularly cutaneous melanoma. The words "prevention" and "prophylaxis" are used interchangeably herein.

Treatment and Vaccination Regimes

A therapeutic regimen may involve either simultaneous (such as co-administration) or sequential (such as a prime-boost) delivery of (i) a polypeptide, nucleic acid or vector of the invention with (ii) one or more further polypeptides, nucleic acids or vectors of the invention and/or (iii) a further component such as a variety of other therapeutically useful compounds or molecules such as antigenic proteins optionally simultaneously administered with adjuvant. Examples of co-administration include homo-lateral co-administration and contra-lateral co-administration. "Simultaneous" administration suitably refers to all components being delivered during the same round of treatment. Suitably all components are administered at the same time (such as simultaneous administration of both DNA and protein), however, one component could be administered within a few minutes (for example, at the same medical appointment or doctor's visit) or within a few hours.

In some embodiments, a "priming" or first administration of a polypeptide, nucleic acid or vector of the invention, is followed by one or more "boosting" or subsequent administrations of a polypeptide, nucleic acid or vector of the invention ("prime and boost" method). In one embodiment the polypeptide, nucleic acid or vector of the invention is used in a prime-boost vaccination regimen. In an embodiment both the prime and boost are of a polypeptide of the invention, the same polypeptide of the invention in each case. In an embodiment both the prime and boost are of a nucleic acid or vector of the invention, the same nucleic acid or vector of the invention in each case. Alternatively, the prime may be performed using a nucleic acid or vector of the invention and the boost performed using a polypeptide of the invention or the prime may be performed using a polypeptide of the invention and the boost performed using a nucleic acid or vector of the invention. Usually the first or "priming" administration and the second or "boosting" administration are given about 1-12 weeks later, or up to 4-6 months later. Subsequent "booster" administrations may be given as frequently as every 1-6 weeks or may be given much later (up to years later).

Antigen Combinations

The polypeptides, nucleic acids or vectors of the invention can be used in combination with one or more other polypeptides or nucleic acids, vectors of the invention and/or with other antigenic polypeptides (or polynucleotides or vectors encoding them) which cause an immune response to be raised against non small cell lung cancer e.g. lung squamous cell carcinoma or melanoma e.g. cutaneous melanoma. These other antigenic polypeptides could be derived from diverse sources. For non small cell lung cancer applications they could include PRAME, NY-ESO-1, MAGE-A3, and MUC1. For melanoma applications they could include well-described melanoma-associated antigens, such as GPR143, PRAME, MAGE-A3 or pMel (gp100). Alternatively they could include other types of melanoma antigens, including patient-specific neoantigens (Lauss et al. (2017). Nature Communications, 8(1), 1738. http://doi.org/10.1038/s41467-017-01460-0), retained-intron neoantigens (Smart et al. (2018). Nature Biotechnology. http://doi.org/10.1038/nbt.4239), spliced variant neoantigens (Hoyos et al., Cancer Cell, 34(2), 181-183. http://doi.org/10.1016/j.ccell.2018.07.008; Kahles et al. (2018). Cancer Cell, 34(2), 211-224.e6. http://doi.org/10.1016/j.ccell.2018.07.001), melanoma antigens that fit within the category known as antigens encoding T cell epitopes associated with impaired peptide processing (TIEPPs, Gigoux, M., & Wolchok, J. (2018). JEM, 215, 2233, Marijt et al. (2018). JEM 215, 2325), or to-be discovered neoantigens (including CLT antigens).

It will be understood that references to "non small cell lung cancer applications" are references to embodiments employing the polypeptides of SEQ ID NOs 1, 2, 3 or 4 or the polynucleotides of SEQ ID Nos. 5, 6, 7 or 8 and related aspects (variants, immunogenic fragments etc as described herein) suitable for use in the treatment or prophylaxis of non small cell lung cancer. References to "melanoma applications" are references to embodiments employing the polypeptides of SEQ ID NOs 1 or 3 or the polynucleotides of SEQ ID Nos. 5 or 7 and related aspects (variants, immunogenic fragments etc as described herein) suitable for use in the treatment or prophylaxis of melanoma.

In addition, the antigenic peptides from these various sources could also be combined with (i) non-specific immunostimulant/adjuvant species and/or (ii) an antigen, e.g. comprising universal CD4 helper epitopes, known to elicit strong CD4 helper T cells (delivered as a polypeptides, or as polynucleotides or vectors encoding these CD4 antigens), to amplify the anti-non small cell lung cancer specific or anti-melanoma-specific responses elicited by co-administered antigens.

Different polypeptides, nucleic acids or vectors may be formulated in the same formulation or in separate formulations. Alternatively, polypeptides may be provided as fusion proteins in which a polypeptide of the invention is fused to a second or further polypeptide (see below).

Nucleic acids may be provided which encode the aforementioned fusion proteins.

More generally, when two or more components are utilised in combination, the components could be presented, for example:

(1) as two or more individual antigenic polypeptide components;

(2) as a fusion protein comprising both (or further) polypeptide components;

(3) as one or more polypeptide and one or more polynucleotide component;

(4) as two or more individual polynucleotide components;

(5) as a single polynucleotide encoding two or more individual polypeptide components; or (6) as a single polynucleotide encoding a fusion protein comprising both (or further) polypeptide components.

For convenience, it is often desirable that when a number of components are present they are contained within a single fusion protein or a polynucleotide encoding a single fusion protein (see below). In one embodiment of the invention all components are provided as polypeptides (e.g., within a single fusion protein). In an alternative embodiment of the invention all components are provided as polynucleotides (e.g., a single polynucleotide, such as one encoding a single fusion protein).

Fusion Proteins

As an embodiment of the above discussion of antigen combinations, the invention also provides an isolated polypeptide according to the invention fused to a second or further polypeptide of the invention (herein after a "combination polypeptide of the invention"), by creating nucleic acid constructs that fuse together the sequences encoding the individual antigens. Combination polypeptides of the invention are expected to have the utilities described herein for polypeptides of the invention, and may have the advantage of superior immunogenic or vaccine activity or prophylactic or therapeutic effect (including increasing the breadth and depth of responses), and may be especially valuable in an outbred population. Fusions of polypeptides of the invention may also provide the benefit of increasing the efficiency of construction and manufacture of vaccine antigens and/or vectored vaccines (including nucleic acid vaccines).

As described above in the Antigen Combinations section, polypeptides of the invention and combination polypeptides of the invention may also be fused to polypeptide sequences which are not polypeptides of the invention, including one or more of:

(a) other polypeptides which are non small cell lung cancer associated antigens (e.g., PRAME, NY-ESO-1, MAGE-A3, and MUC1) or, in the case of melanoma applications, melanoma associated antigens (e.g., GPR143, PRAME, MAGE-A3 and pMel (gp100) referred to supra) and thus potentially useful as immunogenic sequences in a vaccine; and (b) polypeptide sequences which are capable of enhancing an immune response (i.e. immunostimulant sequences).

(c) Polypeptide sequences, e.g. comprising universal CD4 helper epitopes, which are capable of providing strong CD4+ help to increase CD8+ T cell responses to CLT antigen epitopes.

The invention also provides nucleic acids encoding the aforementioned fusion proteins and other aspects of the invention (vectors, compositions, cells etc) mutatis mutandis as for the polypeptides of the invention.

CLT Antigen-Binding Polypeptides

Antigen-binding polypeptides which are immunospecific for tumor-expressed antigens (polypeptides of the invention) may be designed to recruit cytolytic cells to antigen-decorated tumor cells, mediating their destruction. One such mechanism of recruitment of cytolytic cells by antigen-binding polypeptides is known as antibody-dependent cell-mediated cytotoxicity (ADCC). Thus the invention provides an antigen-binding polypeptide which is immunospecific for a polypeptide of the invention. Antigen-binding polypeptides including antibodies such as monoclonal antibodies and fragments thereof e.g., domain antibodies, Fab fragments, Fv fragments, and VHH fragments which may produced in a non-human animal species (e.g., rodent or camelid) and humanised or may be produced in a non-human species (e.g., rodent genetically modified to have a human immune system).

Antigen-binding polypeptides may be produced by methods well known to a skilled person. For example, monoclonal antibodies can be produced using hybridoma technology, by fusing a specific antibody-producing B cell with a myeloma (B cell cancer) cell that is selected for its ability to grow in tissue culture and for an absence of antibody chain synthesis (Kohler and Milstein, 1975, Nature 256(5517): 495-497 and Nelson et al., 2000 (Jun), Mol Pathol. 53(3): 111-7 herein incorporated by reference in their entirety).

A monoclonal antibody directed against a determined antigen can, for example, be obtained by:

a) immortalizing lymphocytes obtained from the peripheral blood of an animal (including a human) previously immunized/exposed with a determined antigen, with an immortal cell and preferably with myeloma cells, in order to form a hybridoma, b) culturing the immortalized cells (hybridoma) formed and recovering the cells producing the antibodies having the desired specificity.

Monoclonal antibodies can be obtained by a process comprising the steps of:

a) cloning into vectors, especially into phages and more particularly filamentous bacteriophages, DNA or cDNA sequences obtained from lymphocytes especially peripheral blood lymphocytes of an animal (suitably previously immunized with determined antigens), b) transforming prokaryotic cells with the above vectors in conditions allowing the production of the antibodies, c) selecting the antibodies by subjecting them to antigen-affinity selection, d) recovering the antibodies having the desired specificity e) expressing antibody-encoding nucleic acid molecules obtained from B cells of patients exposed to antigens, or animals experimentally immunized with antigens.

The selected antibodies may then be produced using conventional recombinant protein production technology (e.g., from genetically engineered CHO cells).

The invention provides an isolated antigen-binding polypeptide which is immunospecific for a polypeptide of the invention. Suitably, the antigen-binding polypeptide is a monoclonal antibody or a fragment thereof.

In certain embodiments, the antigen-binding polypeptide is coupled to a cytotoxic moiety. Example cytotoxic moieties include the Fc domain of an antibody, which will recruit Fc receptor-bearing cells facilitating ADCC. Alternatively, the antigen-binding polypeptide may be linked to a biological toxin, or a cytotoxic chemical.

Another important class of antigen-binding polypeptides include T-cell receptor (TCR)-derived molecules that bind to HLA-displayed fragments of the antigens of this invention. In this embodiment, TCR-based biologicals (including TCRs derived directly from patients, or specifically manipulated, high-affinity TCRs) that recognize CLT antigens (or derivatives thereof) on the surface of tumor cells may also include a targeting moiety which recognizes a component on a T cell (or another class of immune cell) that attract these immune cells to tumors, providing therapeutic benefit. In some embodiments, the targeting moiety may also stimulate beneficial activities (including cytolytic activities) of the redirected immune cells.

Thus, in an embodiment, the antigen-binding polypeptide is immunospecific for an HLA-bound polypeptide that is or is part of a polypeptide of the invention. For example, the antigen-binding polypeptide is a T-cell receptor.

In an embodiment, an antigen-binding polypeptide of the invention may be coupled to another polypeptide that is capable of binding to cytotoxic cells or other immune components in a subject.

In an embodiment, the antigen-binding polypeptide is for use in medicine.

In an embodiment, there is provided a pharmaceutical composition comprising an antigen-binding polypeptide of the invention together with a pharmaceutically acceptable carrier. Such a composition may be a sterile composition suitable for parenteral administration. See e.g., disclosure of pharmaceutical compositions supra.

There is provided by the invention a method of treating a human suffering from cancer wherein the cells of the cancer express a sequence selected from SEQ ID NOs. 1-2 and immunogenic fragments and variants of any one thereof, or of preventing a human from suffering from cancer wherein the cells of the cancer would express a sequence selected from SEQ ID NOs. 1-2 and immunogenic fragments and variants of any one thereof, which comprises administering to said human an antigen-binding polypeptide or composition comprising said antigen-binding polypeptide of the invention.

In an embodiment, there is provided an antigen-binding polypeptide of the invention, which may be coupled to a cytotoxic moiety, or composition comprising said antigen-binding polypeptide of the invention for use in treating or preventing cancer in a human, wherein the cells of the cancer express a corresponding sequence selected from SEQ ID NOs. 1-2 and immunogenic fragments of any one thereof.

Suitably in any of the above embodiments, the cancer is non small cell lung cancer particularly lung squamous cell carcinoma.

In an embodiment, there is provided a method or an antigen-binding polypeptide or composition for use according to the invention wherein the polypeptide comprises a sequence selected from:

(a) the sequence of SEQ ID NO. 1; and (b) a variant of the sequences of (a); and (c) an immunogenic fragment of the sequences of (a).

and for example the polypeptide comprises or consists of a sequence of SEQ ID NO. 3 and for example the nucleic acid comprises or consists of a sequence selected from SEQ ID NOs. 5 or 7;

and wherein the cancer is melanoma, particularly cutaneous melanoma.

Antigen-binding polypeptides (such as antibodies or fragments thereof may be administered ata dose of e.g. 5-1000 mg e.g. 25-500 mg e.g. 100-300 mg e.g. ca. 200 mg.

Cell Therapies to Facilitate Antigen Presentation In Vivo

Any of a variety of cellular delivery vehicles may be employed within pharmaceutical compositions to facilitate production of an antigen-specific immune response. Thus the invention provides a cell which is an isolated antigen presenting cell modified by ex vivo loading with a polypeptide of the invention or genetically engineered to express the polypeptide of the invention (herein after referred to as a "APC of the invention"). Antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response and/or to be immunologically compatible with the receiver (i.e., matched HLA haplotype). APCs may generally be isolated from any of a variety of biological fluids and organs, and may be autologous, allogeneic, syngeneic or xenogeneic cells.

Certain preferred embodiments of the present invention use dendritic cells or progenitors thereof as APCs. Thus, in an embodiment, the APC of the invention is a dendritic cell. Dendritic cells are highly potent APCs (Banchereau & Steinman, 1998, *Nature,* 392:245-251) and have been shown to be effective as a physiological adjuvant for eliciting prophylactic or therapeutic immunity (see Timmerman & Levy, 1999, *Ann. Rev. Med.* 50:507-529). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course be engineered to express specific cell-surface receptors or ligands that are not commonly found on dendritic cells in vivo or ex vivo, and such modified dendritic cells are contemplated by the present invention. As an alternative to dendritic cells, antigen-loaded secreted vesicles (called exosomes) may be used within an immunogenic composition (see Zitvogel et al., 1998, *Nature Med.* 4:594-600). Thus, in an embodiment, there is provided an exosome loaded with a polypeptide of the invention.

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34-positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorised as "immature" and "mature" cells, which allows a simple way to discriminate between two well-characterised phenotypes. However, this nomenclature should not be construed to exclude all possible intermediate stages of differentiation. Immature dendritic cells are characterised as APCs with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may also be genetically engineered e.g., transfected with a polynucleotide encoding a protein (or portion or other variant thereof) such that the polypeptide is expressed on the cell surface. Such transfection may take place ex vivo, and a pharmaceutical composition comprising such transfected cells may then be used, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., 1997, *Immunology and Cell Biology* 75:456-460. Antigen loading of dendritic cells may be achieved by incubating dendritic cells or progenitor cells with the polypeptide, DNA (e.g., a plasmid vector) or RNA; or with antigen-expressing recombinant bacteria or viruses (e.g., an adenovirus, adeno-associated virus (AAV) (e.g., AAV type 5 and type 2), alphavirus (e.g., Venezuelan equine encephalitis virus (VEEV), Sindbis virus (SIN), Semliki Forest virus (SFV), herpes virus, arenavirus (e.g., lymphocytic choriomeningitis virus (LCMV)), measles virus, poxvirus (such as modified vaccinia Ankara (MVA) or fowlpox), paramyxovirus, lentivirus, or rhabdovirus (such as vesicular stomatitis virus (VSV)). Prior to loading, the polypeptides may be covalently conjugated to an immunological partner that provides T cell help (e.g., a carrier molecule). Alternatively, a dendritic cell may be pulsed with a non-conjugated immunological partner, separately or in the presence of the polypeptide.

The invention provides for delivery of specifically designed short, chemically synthesized epitope-encoded fragments of polypeptide antigens to antigen presenting cells. Those skilled in the art will realize that these types of molecules, also known as synthetic long peptides (SLPs) provide a therapeutic platform for using the antigenic polypeptides of this invention to stimulate (or load) cells in vitro (Gornati et al., 2018, Front. Imm, 9:1484), or as a method of introducing polypeptide antigen into antigen-presenting cells in vivo (Melief & van der Burg, 2008, Nat Rev Cancer, 8:351-60).

In an embodiment, there is provided a pharmaceutical composition comprising an antigen-presenting cell of the invention, which is suitably a dendritic cell, together with a pharmaceutically acceptable carrier. Such a composition may be a sterile composition suitable for parenteral administration. See e.g., disclosure of pharmaceutical compositions supra.

In an embodiment, there is provided an antigen-presenting cell of the invention, which is suitably a dendritic cell, for use in medicine.

There is also provided a method of treating a human suffering from cancer wherein the cells of the cancer express a sequence selected from SEQ ID NOs. 1-2 and immunogenic fragments and variants of any one thereof, or of preventing a human from suffering from cancer wherein the cells of the cancer would express a sequence selected from SEQ ID NOs. 1-2 and immunogenic fragments and variants of any one thereof, which comprises administering to said human said antigen presenting cell of the invention, which is suitably a dendritic cell, or composition comprising said antigen presenting cell of the invention.

In an embodiment, there is provided an antigen presenting cell of the invention, which is suitably a dendritic cell, or composition comprising said antigen presenting cell of the invention for use in treating or preventing cancer in a human, wherein the cells of the cancer express a corresponding sequence selected from SEQ ID NOs. 1-2 and immunogenic fragments of any one thereof.

In an emodiment, there is provided a pharmaceutical composition comprising an exosome of the invention together with a pharmaceutically acceptable carrier. Such a composition may be a sterile composition suitable for parenteral administration. See e.g., disclosure of pharmaceutical compositions supra. Compositions may optionally comprise immunostimulants—see disclosure of immunostimulants supra.

In an embodiment, there is provided an exosome of the invention for use in medicine.

There is also provided a method of treating a human suffering from cancer wherein the cells of the cancer express a sequence selected from SEQ ID NOs. 1-2 and immunogenic fragments and variants of any one thereof, or of preventing a human from suffering from cancer wherein the cells of the cancer would express a sequence selected from SEQ ID NOs. 1-2 and immunogenic fragments and variants of any one thereof, which comprises administering to said human said exosome if the invention or composition comprising said exosome of the invention.

In an embodiment, there is provided an exosome of the invention or composition comprising said exosome of the invention for use in treating or preventing cancer in a human, wherein the cells of the cancer express a corresponding sequence selected from SEQ ID NOs. 1-2 and immunogenic fragments of any one thereof. In any one of the above embodiments, suitably the cancer is non small cell lung cancer particularly lung squamous cell carcinoma, or, in the case of melanoma applications, melanoma particularly cutaneous melanoma.

Stimulated T-Cell Therapies

In addition to in vivo or ex vivo APC-mediated production of T-cells immunospecific for polypeptides of the invention, autologous or non-autologous T-cells may be isolated from a subject, e.g., from peripheral blood, umbilical cord blood and/or by apheresis, and stimulated in the presence of a tumor-associated antigens which are loaded onto MHC molecules (signal 1) of APC cells, to induce proliferation of T-cells with a TCR immunospecific for this antigen.

Successful T-cell activation requires the binding of the costimulatory surface molecules B7 and CD28 on antigen-presenting cells and T cells, respectively (signal 2). To achieve optimal T-cell activation, both signals 1 and 2 are required. Conversely, antigenic peptide stimulation (signal 1) in the absence of costimulation (signal 2) cannot induce full T-cell activation, and may result in T-cell tolerance. In addition to costimulatory molecules, there are also inhibitory molecules, such as CTLA-4 and PD-1, which induce signals to prevent T-cell activation.

Autologous or non-autolgous T-cells may therefore be stimulated in the presence of a polypeptide of the invention, and expanded and transferred back to the patient at risk of or suffering from cancer whose cancer cells express a corresponding polypeptide of the invention provided that the antigen-specific TCRs will recognize the antigen presented by the patient's MHC, where they will target and induce the killing of cells of said cancer which express said corresponding polypeptide.

In an embodiment, there is provided a polypeptide, nucleic acid, vector or composition of the invention for use in the ex vivo stimulation and/or amplification of T-cells derived from a human suffering from cancer, for subsequent reintroduction of said stimulated and/or amplified T cells into the said human for the treatment of the said cancer in the said human.

The invention provides a method of treatment of cancer in a human, wherein the cells of the cancer express a sequence selected from SEQ ID NOs. 1-2 and immunogenic fragments and variants of any one thereof, which comprises taking from said human a population of white blood cells comprising at least T-cells optionally with antigen-presenting cells, stimulating and/or amplifying said T-cells in the presence of a corresponding polypeptide, nucleic acid, vector or composition of the invention, and reintroducing some or all of said white blood cells comprising at least stimulated and/or amplified T cells T-cells into the human.

In any one of the above embodiments, suitably the cancer is non small cell lung cancer particularly lung squamous cell carcinoma, or, in the case of melanoma applications, melanoma particularly cutaneous melanoma.

In an embodiment, there is provided a process for preparing a T-cell population which is cytotoxic for cancer cells which express a sequence selected from SEQ ID NOs. 1-2 and immunogenic fragments and variants of any one thereof which comprises (a) obtaining T-cells and antigen-presenting cells from a cancer patient and (ii) stimulating and amplifying the T-cell population ex vivo with a corresponding polypeptide, nucleic acid, vector or composition of the invention.

By "corresponding" in this context is meant that if the cancer cells express, say, SEQ ID NO. A (A being one of SEQ ID NOs. 1-2) or a variant or immunogenic fragment thereof then the T-cell population is stimulated and amplified ex vivo with SEQ ID NO. A or a variant or immunogenic fragment thereof in the form of a polypeptide, nucleic acid or vector, or a composition containing one of the foregoing.

For example, in such processes, the culturing and expanding is performed in the presence of dendritic cells. The dendritic cells may be transfected with a nucleic acid molecule or with a vector of the invention and express a polypeptide of the invention.

The invention provides a T-cell population obtainable by any of the aforementioned processes (hereinafter a T-cell population of the invention).

In an embodiment, there is provided a cell which is a T-cell which has been stimulated with a polypeptide, nucleic acid, vector or composition of the invention (hereinafter a T-cell of the invention).

In an embodiment, there is provided a pharmaceutical composition comprising a T-cell population or a T-cell of the invention together with a pharmaceutically acceptable carrier. Such a composition may, for example, be a sterile composition suitable for parenteral administration.

In an embodiment, there is provided a T-cell population or T-cell of the invention for use in medicine.

There is also provided a method of treating a human suffering from cancer wherein the cells of the cancer express a sequence selected from SEQ ID NOs. 1-2 and immunogenic fragments and variants of any one thereof, or of preventing a human from suffering from cancer wherein the cells of the cancer would express a sequence selected from SEQ ID NOs. 1-2 and immunogenic fragments and variants of any one thereof, which comprises administering to said human said T-cell population or T-cell of the invention or composition comprising said T-cell population or T-cell of the invention.

In an embodiment, there is provided a T-cell population of the invention, T-cell of the invention or composition comprising said T-cell population or T-cell of the invention for use in treating or preventing cancer in a human, wherein the cells of the cancer express a corresponding sequence selected from SEQ ID NOs. 1-2 and immunogenic fragments of any one thereof. In any one of the above embodiments, suitably the cancer is non small cell lung cancer particularly lung squamous cell carcinoma, or, in the case of melanoma applications, melanoma particularly cutaneous melanoma.

In an embodiment, there is provided a process, a method or a T-cell population, T-cell, antigen presenting cell, exosome or composition for use according to the invention wherein the polypeptide comprises a sequence selected from:

(a) the sequence of SEQ ID NO. 1 and
  (b) a variant of the sequences of (a); and
  (c) an immunogenic fragment of the sequences of (a).
  and for example the polypeptide comprises or consists of SEQ ID NO. 3 and for example the nucleic acid comprises or consists of a sequence selected from SEQ ID NOs. 4 or7;
  and wherein the cancer is melanoma, particularly cutaneous melanoma.

Engineered Immune Cell Therapies

Derivatives of all types of CLT antigen-binding polypeptides described above, including TCRs or TCR mimetics (see Dubrovsky et al., 2016, Oncoimmunology) that recognize CLT antigen-derived peptides complexed to human HLA molecules, may be engineered to be expressed on the surface of T cells (autologous or non-autologous), which can then be administered as adoptive T cell therapies to treat cancer.

These derivatives fit within the category of "chimeric antigen receptors (CARs)," which, as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. CARs may direct specificity of the cell to a tumor associated antigen, a polypeptide of the invention, wherein the polypeptide is HLA-bound.

Another approach to treating cancer in a patient is to genetically modify T-cells to target antigens expressed on tumor cells, via the expression of chimeric antigen receptors (CARs). This technology is reviewed in Wendell & June, 2017, Cell, 168: 724-740 (incorporated by reference in its entirety).

Such CAR T-cells may be produced by the method of obtaining a sample of cells from the subject, e.g., from peripheral blood, umbilical cord blood and/or by apheresis, wherein said sample comprises T-cells or T-cell progenitors, and transfecting said cells with a nucleic acid encoding a chimeric T-cell receptor (CAR) which is immunospecific for the polypeptide of the invention, wherein the polypeptide is HLA-bound. Such nucleic acid will be capable of integration into the genome of the cells, and the cells may be administered in an effective amount the subject to provide a T-cell response against cells expressing a polypeptide of the invention. For example, the sample of cells from the subject may be collected.

It is understood that cells used to produce said CAR-expressing T-cells may be autologous or non-autologous.

Transgenic CAR-expressing T cells may have expression of an endogenous T-cell receptor and/or endogenous HLA inactivated. For example, the cells may be engineered to eliminate expression of endogenous alpha/beta T-cell receptor (TCR).

Methods of transfecting of cells are well known in the art, but highly efficient transfection methods such as electroporation may be employed. For example, nucleic acids or vectors of the invention expressing the CAR constructs may be introduced into cells using a nucleofection apparatus.

The cell population for CAR-expressing T-cells may be enriched after transfection of the cells. For example, the cells expressing the CAR may be sorted from those which do not (e.g., via FACS) by use of an antigen bound by the CAR or a CAR-binding antibody. Alternatively, the enrichment step comprises depletion of the non-T-cells or depletion of cells that lack CAR expression. For example, CD56+ cells can be depleted from a culture population.

The population of transgenic CAR-expressing cells may be cultured ex vivo in a medium that selectively enhances proliferation of CAR-expressing T-cells. Therefore, the CAR-expressing T cell may be expanded ex vivo.

A sample of CAR cells may be preserved (or maintained in culture). For example, a sample may be cryopreserved for later expansion or analysis.

CAR-expressing T cells may be employed in combination with other therapeutics, for example checkpoint inhibitors including PD-L1 antagonists.

In an embodiment, there is provided a cytotoxic cell that has been engineered to express any of the above antigen-binding polypeptides on its surface. Suitably, the cytotoxic cell is a T-cell.

In an embodiment, there is provided a cytotoxic cell, which is suitably a T-cell, engineered to express any of the above antigen-binding polypeptides on its surface, for use in medicine The invention provides a pharmaceutical composition comprising a cytotoxic cell of the invention, which is suitably a T-cell.

There is provided a method of treating a human patient suffering from cancer wherein the cells of the cancer express a sequence selected from SEQ ID NOs. 1-2 and immunogenic fragments and variants of any one thereof, or of preventing a human from suffering from cancer which cancer would express a sequence selected from SEQ ID NOs. 1-2 and immunogenic fragments and variants of any one thereof, which method comprises administering to said human a cytotoxic cell of the invention, which is suitably a T-cell.

In an embodiment the cytotoxic cell of the invention, which is suitably a T-cell, is for use in treating or preventing cancer in a human, wherein the cells of the cancer express a corresponding sequence selected from SEQ ID NOs. 1-2 and immunogenic fragments of any one thereof.

Combination Therapies

Methods of treating cancer according to the invention may be performed in combination with other therapies, especially checkpoint inhibitors and interferons.

The polypeptides, nucleic acids, vectors, antigen-binding polypeptide and adoptive cell therapies (APC and T cell-based) can be used in combination with other components designed to enhance their immunogenicity, for example, to improve the magnitude and/or breadth of the elicited immune response, or provide other activities (e.g., activation of other aspects of the innate or adaptive immune response, or destruction of tumor cells).

Accordingly, the invention provides a composition of the invention (i.e. an immunogenic, vaccine or pharmaceutical composition) or a kit of several such compositions comprising a polypeptide, nucleic acid or vector of the invention together with a pharmaceutically acceptable carrier; and (i) one or more further immunogenic or immunostimulant polypeptides (e.g., interferons, IL-12, checkpoint blockade molecules or nucleic acids encoding such, or vectors comprising such nucleic acids), (ii) small molecules (e.g., HDAC inhibitors or other drugs that modify the epigenetic profile of cancer cells) or biologicals (delivered as polypeptides or nucleic acids encoding such, or vectors comprising such nucleic acids) that will enhance the translation and/or presentation of the polypeptide products that are the subject of this invention.

Checkpoint inhibitors, which block normal proteins on cancer cells, or the proteins on the T cells that respond to them, may be a particularly important class of drugs to combine with CLT-antigen based therapies, since these inhibitors seek to overcome one of cancers main defences against an immune system attack.

Thus, an aspect of the invention includes administering a polypeptide, nucleic acid, vector, antigen-binding polypeptide, composition, T-cell, T-cell population, or antigen presenting cell of the present invention in combination with a checkpoint inhibitor. Example check point inhibitors are selected from PD-1 inhibitors, such as pembrolizumab, (Keytruda) and nivolumab (Opdivo), PD-L1 inhibitors, such as atezolizumab (Tecentriq), avelumab (Bavencio) and durvalumab (Imfinzi) and CTLA-4 inhibitors such as ipilimumab (Yervoy).

Interferons (e.g., alpha, beta and gamma) are a family of proteins the body makes in very small amounts. Interferons may slow down or stop the cancer cells dividing, reduce the ability of the cancer cells to protect themselves from the immune system and/or enhance multiple aspects of the adaptive immune system. Interferons are typically administered as a subcutaneous injection in, for example the thigh or abdomen.

Thus, an aspect of the invention includes administering a polypeptide, nucleic acid, vector, antigen-binding polypeptide or composition of the present invention in combination with interferon e.g., interferon alpha.

Different modes of the invention may also be combined, for example polypeptides, nucleic acids and vectors of the invention may be combined with an APC, a T-cell or a T-cell population of the invention (discussed infra).

One or more modes of the invention may also be combined with conventional anti-cancer chemotherapy and/or radiation.

Diagnostics

In another aspect, the invention provides methods for using one or more of the polypeptides or nucleic acid of the invention to diagnose cancer, particularly non small cell lung cancer e.g. lung squamous cell carcinoma or melanoma e.g. cutaneous melanoma, or to diagnose human subjects suitable for treatment by polypeptides, nucleic acids, vectors, antigen-binding polypeptides, adoptive cell therapies, or compositions of the invention.

Thus the invention provides a method of diagnosing that a human suffering from cancer, comprising the steps of: determining if the cells of said cancer express a polypeptide sequence selected from SEQ ID NOs. 1-2 and immunogenic fragments or variants of any one thereof (e.g. selected from the sequences of SEQ ID NOs. 3-4); or a nucleic acid encoding said polypeptide sequence (e.g. selected from the sequences of SEQ ID NOs. 5-6 and SEQ ID NOs. 7-8), and diagnosing said human as suffering from cancer if said polypeptide or corresponding nucleic acid is overexpressed in said cancer cells.

The invention provides a method of diagnosing that a human suffering from cancer which is non small cell lung cancer e.g. lung squamous cell carcinoma, comprising the steps of: determining if the cells of said cancer express a polypeptide sequence selected from SEQ ID NO. 2 and immunogenic fragments or variants thereof; or a nucleic acid encoding said polypeptide sequence, and diagnosing said human as suffering from cancer which is small cell lung cancer e.g. lung squamous cell carcinoma if said polypeptide or corresponding nucleic acid is overexpressed in said cancer cells.

The invention provides a method of diagnosing that a human suffering from cancer which is non small cell lung cancer e.g. lung squamous cell carcinoma or melanoma e.g. cutaneous melanoma, comprising the steps of: determining if the cells of said cancer express a polypeptide sequence selected from SEQ ID NO. 1 and immunogenic fragments or variants thereof; or a nucleic acid encoding said polypeptide sequence, and diagnosing said human as suffering from cancer which is small cell lung cancer e.g. lung squamous cell carcinoma if said polypeptide or corresponding nucleic acid is overexpressed in said cancer cells.

The invention provides a method of diagnosing that a human suffering from cancer which is non small cell lung cancer e.g. lung squamous cell carcinoma or melanoma, particularly cutaneous melanoma, comprising the steps of: determining if the cells of said cancer express a polypeptide sequence selected from SEQ ID NO. 1 and immunogenic fragments or variants of any one thereof; or a nucleic acid encoding said polypeptide sequence, and diagnosing said human as suffering from cancer which is non small cell lung cancer e.g. lung squamous cell carcinoma or melanoma, particularly cutaneous melanoma if said polypeptide or corresponding nucleic acid is overexpressed in said cancer cells.

As used herein, "overexpressed" in cancer cells means that the level of expression in cancer cells is higher than in normal cells.

The overexpression can be determined by reference to the level of the nucleic acid or polypeptide of the invention in a control human subject known not to have the cancer. Thus overexpression indicates that the nucleic acid or polypeptide of the invention is detected at a significantly higher level (e.g., a level which is 30%, 50%, 100% or 500% higher) in the test subject than in the control subject. In case the control human subject has an undetectable level of the nucleic acid or polypeptide of the invention, then the diagnosis can be arrived at by detecting the nucleic acid or polypeptide of the invention.

The invention also provides a method of treating a human suffering from cancer, comprising the steps of:

(a) determining if the cells of said cancer express a polypeptide sequence selected from SEQ ID NOs. 1-2 and immunogenic fragments or variants of any one thereof (e.g. selected from the sequences of SEQ ID NOs. 3-4) or a nucleic acid encoding said polypeptide (e.g. selected from the sequences of SEQ ID NOs. 5-6 and 7-8); and if so (b) administering to said human a corresponding polypeptide, nucleic acid, vector, composition, T-cell population, T-cell, antigen presenting cell, antigen-binding polypeptide or cytotoxic cell of the invention.

There is also provided use of a polypeptide comprising a sequence selected from:

(a) the sequence of any one of SEQ ID NOs. 1-2; or (b) a variant of the sequences of (a); and (c) an immunogenic fragment of the sequences of (a) isolated from the tumor of a human suffering from cancer, or use of a nucleic acid encoding said polypeptide, as a biomarker for the determination of whether said human would be suitable for treatment by a vaccine comprising a corresponding polypeptide, nucleic acid, vector, composition, T-cell population, T-cell, antigen presenting cell, antigen-binding polypeptide or cytotoxic cell of the invention.

Suitably, the cancer is non small cell lung cancer particularly lung squamous cell carcinoma.

The invention also provides a method or use according to the invention wherein the polypeptide comprises a sequence selected from:

(a) the sequence of SEQ ID NO. 1; and (b) a variant of the sequences of (a); and (c) an immunogenic fragment of the sequences of (a).

and for example the polypeptide comprises or consists of a sequence of SEQ ID NO. 3 and for example the nucleic acid comprises or consists of a sequence of SEQ ID NOs. 5 or 7;

and wherein the cancer is melanoma, particularly cutaneous melanoma.

Suitably the polypeptide of the invention has a sequence selected from SEQ ID NOs. 1-2 ora fragment thereof, such as an immunogenic fragment thereof (e.g. selected from the sequences of SEQ ID NOs. 3-4).

Suitably the nucleic acid of the invention has or comprises a sequence selected from any one of SEQ ID NOs. 5-6 or 7-8 or a fragment thereof, such as an immunogenic fragment thereof.

Kits for detecting the presence of nucleic acids are well known. For example, kits comprising at least two oligonucleotides which hybridise to a polynucleotide may be used within a real-time PCR (RT-PCR) reaction to allow the detection and semi-quantification of specific nucleic acids. Such kits may allow the detection of PCR products by the generation of a fluorescent signal as a result of Forster Resonance Energy Transfer (FRET) (for example Tag Man® kits), or upon binding of double stranded DNA (for example, SYBR® Green kits). Some kits (for example, those containing TaqMan® probes whch span the exons of the target DNA) allow the detection and quanitfication of mRNA, for example transcripts encoding nucleic acids of the invention. Assays using certain kits may be set up in a multiplex format to detect multiple nucleic acids simultaneously within a reaction. Kits for the detection of active DNA (namely DNA that carries specific epigenetic signatures indicative of expression) may also be used. Additional components that may be present within such kits include a diagnostic reagent or reporter to facilitate the detection of a nucleic acid of the invention.

Nucleic acids of the invention may also be detected via liquid biopsy, using a sample of blood from a patient. Such a procedure provides a non-invasive alternative to surgical biopsies. Plasma from such blood samples may be isolated and analysed for the presence of nucleic acids of the invention.

Polypeptides of the invention may be detected by means of antigen-specific antibodies in an ELISA type assay to detect polypeptides of the invention in homogenized preparations of patient tumor samples. Alternatively, polypeptides of the invention may be detected by means of immunohistochemical analyses, which identify the presence of the polypeptide antigens by using light microscopy to inspect sections of patient tumor samples that have been stained by using approproiately labeled antibody preparations. As a further alternative, polypeptides of the invention may be detected by means of immunohistochemical analyses, which identify the presence of the polypeptide antigens by using light microscopy to inspect sections of patient tumor samples that have been stained by using approproiately labeled antibody preparations.

Polypeptides of the invention may also be detected by determining whether they are capable of stimulating T-cells raised against the said polypeptide.

Cells of the cancer or tumor e.g., the non small cell lung cancer e.g. lung squamous cell carcinoma or melanoma e.g. cutaneous melanoma may for example be obtained from a biopsy of the cancer e.g., the non small cell lung cancer e.g. lung squamous cell carcinoma or e.g. melanoma e.g. cutaneous melanoma.

A method of treatment of cancer, particularly non small cell lung cancer e.g. lung squamous cell carcinoma or melanoma e.g. cutaneous melanoma, in a human comprises (i) detecting the presence of a nucleic acid or polypeptide according to the invention and (ii) administering to the subject a nucleic acid, polypeptide, vector, cell, T-cell or T-cell population or composition according to the invention (and preferably administering the same nucleic acid or polypeptide or fragment thereof that has been detected).

A method of treatment of cancer, particularly non small cell lung cancer e.g. lung squamous cell carcinoma or melanoma e.g. cutaneous melanoma, in a human also comprises administering to the subject a nucleic acid, polypeptide, vector, cell, T-cell or T-cell population or composition according to the invention, in which subject the presence of a (and preferably the same) nucleic acid or polypeptide according to the invention has been detected.

In particular, the cancer to be diagnosed and if appropriate treated is non small cell lung cancer e.g. lung squamous cell carcinoma or melanoma, e.g. cutaneous melanoma.

Where a polypeptide of the invention of SEQ ID NO. 1 or a fragment thereof is detected then the cancer is expected to be non small cell lung cancer e.g. lung squamous cell carcinoma or melanoma e.g. cutaneous melanoma.

Where a polypeptide of the invention of SEQ ID NO. 2 or a fragment thereof is detected then the cancer is expected to be non small cell lung cancer e.g. lung squamous cell carcinoma.

SPECIFIC EMBODIMENTS

In an embodiment, the CLT antigen polypeptide comprises or consists of SEQ ID NO. 1. Exemplary fragments comprise or consist of SEQ ID NO. 3. Exemplary nucleic acids encoding said polypeptide sequence comprise or consists of SEQ ID NO 5 or SEQ ID NO. 7. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially non small cell lung cancer e.g. lung squamous cell carcinoma or melanoma e.g. cutaneous melanoma. Related methods of diagnosis are also provided.

In an embodiment, the CLT antigen polypeptide comprises or consists of SEQ ID NO. 2. Exemplary fragments comprise or consist of SEQ ID NO. 4. Exemplary nucleic acids encoding said polypeptide sequence comprise or consist of SEQ ID NO. 6 or SEQ ID NO. 8. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially non small cell lung cancer e.g. lung squamous cell carcinoma. Related methods of diagnosis are also provided.

EXAMPLES

Example 1—CLT Identification

The objective was to identify cancer-specific transcripts that entirely or partially consist of LTR elements.

As a first step, we de novo assembled a comprehensive pan-cancer transcriptome. To achieve this, RNA-sequencing reads from 768 patient samples, obtained from The Cancer Genome Atlas (TCGA) consortium to represent a wide variety of cancer types (24 gender-balanced samples from each of 32 cancer types (31 primary and 1 metastatic melanoma); Table S1), were used for genome-guided assembly. The gender-balanced samples (excluding gender-specific tissues) were adapter and quality (Q20) trimmed and length filtered (both reads of the pair n5 nucleotides) using cutadapt (v1.13) (Marcel M., 2011, EMBnet J., 17:3) and kmer-normalized (k=20) using khmer (v2.0) (Crusoe et al., 2015, F1000Res., 4:900) for maximum and minimum depths of 200 and 3, respectively. Reads were mapped to GRCh38 using STAR (2.5.2b) with settings identical to those used across TCGA and passed to Trinity (v2.2.0) (Trinity, Grabherr, M. G., et al., 2011, Nat. Biotechnol., 29:644-52) for a genome-guided assembly with inbuilt in silico depth normalization disabled. The majority of assembly processes were completed within 256GB RAM on 32-core HPC nodes, with failed processes re-run using 1.5TB RAM nodes. Resulting contigs were poly(A)-trimmed (trimpoly within SeqClean v110222) and entropy-filtered (0.7) to remove low-quality and artefactual contigs (bbduk within BBMap v36.2). Per cancer type, the original 24 samples were quasi-mapped to the cleaned assembly using Salmon (v0.8.2 or v0.9.2) (Patro, R., et al., 2017, Nat. Methods, 14:417-419), with contigs found expressed at <0.1 transcripts per million (TPM) being removed. Those remaining were mapped to GRCh38 using GMAP (v161107) (Wu et al., 2005, Bioinf., 21:1859-1875), and contigs not aligning with ≥85% identity over 85%, of their length were removed from the assembly. Finally, assemblies for all cancer types together were flatteed and merged into the longest continuous transcripts using gffread (Cufflinks v2.2.1) (Trapnell et al., 2010, Nat. Biotech., 28:511-515). As this assembly process was specifically designed to enable assessment of repetitive elements, monoexonic transcripts were retained, but flagged. Transcript assembly completeness and quality was assessed by comparison with GENCODE v24basic and MiTranscriptome1 Oyer et al. 2015, Nat. Genet., 47: 199-208). We compiled the list of unique splice sites represented within GENCODE and tested if the splice site was present within the transcriptome assembly within a 2-nucleotide grace window. This process resulted in the identification of 1,001,931 transcripts, 771,006 of which were spliced and 230,925 monoexonic.

Separately, the assembled contigs were overlaid with a genomic repeat sequence annotation to identify transcripts that contain an LTR element. LTR and non-LTR elements were annotated as previously described (Attig et al., 2017, Front. In Microbiol., 8:2489). Briefly, hidden Markov models (HMMs) representing known Human repeat families (Dfam 2.0 library v150923) were used to annotate GRCh38 using RepeatMasker Open-3.0 (Smit, A., R. Hubley, and P. Green, http://www.repeatmasker.org, 1996-2010), configured with nhmmer (Wheeler et al., 2013, Bioinform., 29:2487-2489). HMM-based scanning increases the accuracy of annotation in comparison with BLAST-based methods (Hubley et al., 2016, Nuc. Acid. Res., 44:81-89). RepeatMasker annotates LTR and internal regions separately, thus tabular outputs were parsed to merge adjacent annotations for the same element. This process yielded 181,967 transcripts that contained one or more, complete or partial LTR element.

Transcripts per million (TPM) were estimated for all transcripts using Salmon and expression within each cancer type was compared with expression across 811 healthy tissue samples (healthy tissue-matched controls for all cancer types, where available, from TOGA and, separately from, GTEx (The Genotype-Tissue Expression Consortium, 2015, Science, 348:648-60). Transcripts were considered expressed in cancer if detected at more than 1 TPM in any sample and as cancer-specific if the following criteria were fulfilled: i, expressed in ≥6 of the 24 samples of each cancer type; ii, expressed at <10 TPM in ≥90% of all healthy tissue samples; iii, expressed in the cancer type of interest ≥3× the median expression in any control tissue type; and iv, expressed in the cancer type of interest ≤3×the 90th percentile of the respective healthy tissue, where available.

The list of cancer-specific transcripts was then intersected with the list of transcripts containing complete or partial LTR elements to produce a list of 5,923 transcripts that fulfilled all criteria (referred to as CLTs for Cancer-specific LTR element-spanning Transcripts).

Further curation was carried out on 229 CLTs specifically expressed in lung squamous cell carcinoma to exclude potentially misassembled contigs and those corresponding to the assembly of cellular genes. Additional manual assessment was conducted to ensure that splicing patterns were supported by the original RNA-sequencing reads from lung squamous cell carcinoma. CLTs were additionally triaged such that those where the median expression in any GTEx normal tissue exceeded 1 TPM were discarded.

Within the 229 CLTs for lung squamous cell carcinoma, 45 CLTs passed these filters.

Further curation was carried out on 403 CLTs specifically expressed in melanoma to exclude potentially misassembled contigs and those corresponding to the assembly of cellular genes. Additional manual assessment was conducted to ensure that splicing patterns were supported by the original RNA-sequencing reads from melanoma. CLTs were additionally triaged such that those where the median expression in any GTEx normal tissue exceeded 1 TPM were discarded.

Within the 403 CLTs for cutaneous melanoma, 97 CLTs passed these filters.

Among the 45 filtered CLTs specific for lung squamous cell carcinoma, 3 were also present in the 97 filtered CLTs specific for melanoma.

Example 2—Immunopeptidomic Analysis

Mass spectrometry (MS)-based immunopeptidomics analysis is a powerful technology that allows for the direct identification of specific peptides associated with HLA molecules (HLAp) and presented on the cell surface. The technique consists of affinity purification of the HLAp from biological samples such as cells or tissues by anti-HLA antibody capture. The isolated HLA molecules and bound peptides are then separated from each other and the eluted peptides are analyzed by nano-ultra performance liquid chromatography coupled to mass spectrometry (nUPLC-MS) (Freudenmann et al., 2018, Immunology 154(3):331-345). In the mass spectrometer, specific peptides of defined charge-to-mass ratio (m/z) are selected, isolated, fragmented, and then subjected to a second round of mass spectrometry (MS/MS) to reveal the m/z of the resulting fragment ions. The fragmentation spectra (MS/MS) can then be interrogated to precisely identify the amino acid sequence of the selected peptide that gave rise to the detected fragment ions.

MS/MS spectral interpretation and subsequent peptide sequence identification relies on the match between experimental data and theoretical spectra created from peptide sequences found in a reference database. Although it is possible to search MS data by using pre-defined lists corresponding to all open reading frames (ORFs) derived from the known transcriptome or even the entire genome (Nesvizhskii et al., 2014, Nat. Methods 11: 1114-1125), interrogating these very large sequence databases leads to very high false discovery rates (FDR) that limit the identification of presented peptides. Further technical issues (e.g., mass of leucine=mass of isoleucine), and theoretical issues (e.g., peptide splicing (Liepe, et al., 2016, *Science* 354 (6310): 354-358)) increase the limitations associated with use of very large databases, such as those produced from the known transcriptome or entire genome. Thus, in practice, it is exceptionally difficult to perform accurate immunopeptidomics analyses to identify novel antigens without reference to a well-defined set of potential polypeptide sequences (Li, et al., 2016, *BMC Genomics* 17 (Suppl) 13):1031).

To discover if peptides presented in lung tumor tissues were found in our lung squamous cell carcinoma CLTs, we constructed a database of all predicted polypeptide sequences (ORFs) of ≥10 residues from the 45 lung squamous cell carcinoma CLTs of Example 1, to allow us to interrogate these ORFs with immunopeptidomic data. This yielded 988 ORFs ranging in length from 10 to 468 amino acids.

Bulik-Sullivan et al. (*Nature Biotechnology* 37:55-63 (2019); database: MassIVE Archive (http://massive.ucs-d.edu), accession code MSV000082648) generated MS/MS data from HLA class I-bound peptide samples derived from diverse cancers, including 39 lung tumors of multiple sub-types including: 11 NSCLC, 2 lung squamous cell, 10 NSCLC adenocarcinomas, 4 NSCLC—Large Cell Carcinomas, 10 NSCLC—Squamous cell cancers, 1 NSCLC—Papillary Adeno, and 1 tumor with no reported subtype. Bulik-Sullivan et al. used this lung cancer dataset as part of the larger dataset, that was used to train (and test) an algorithm to predict HLA class I peptide presentation, for the purpose of prioritizing somatic neoantigens for use in cancer vaccines. As expected, the Bulik-Sullivan lung tumor dataset also included large numbers of peptides that matched to known human proteins.

The inventors procured frozen tumor tissue from 4 patients diagnosed with lung squamous cell carcinoma. Samples between 0.15-0.4 g were homogenized, the lysate was centrifugate at high speed and the cleared lysate was mixed with protein A (ProA) beads covalently linked to an anti-human HLA class I monoclonal antibody (W6/32). The mixture was incubated overnight at 4° C. to improve HLA Class I molecule binding to antibody (Ternette et al., 2018 *Proteomics* 18, 1700465). The HLA Class I-bound peptides were eluted from the antibody by using 10% acetic acid, and the peptides were then separated from other high molecular mass components using reversed-phase column chromatography (Ternette et al., 2018). The purified, eluted peptides were subjected to nUPLC-MS, and specific peptides of defined charge-to-mass ratio (m/z) were selected within the mass spectrometer, isolated, fragmented, and subjected to a second round of mass spectrometry (MS/MS) to reveal the m/z of the resulting fragment ions (Ternette et al., 2018), producing an MS/MS dataset corresponding to the immunopeptidome for each of these tumor samples.

By applying detailed knowledge of immunopeptidomics evaluation, the inventors interrogated the spectra from the MSV000082648 HLA Class I dataset for the 39 lung tumor samples of Bulik-Sullivan et al. and the spectra of the HLA-Class I dataset for the 4 lung squamous cell carcinoma tumors prepared by the inventors with the lung squamous cell carcinoma CLT-derived ORFs (of Example 1; concatenated for each CLT) alongside all polypeptide sequences found in the human proteome (UniProt) using PEAKS™ software (v8.5 and vX, Bioinformatics Solutions Inc). Since the majority of HLA Class I-bound peptides found in cells are derived from constitutively expressed proteins, the simultaneous interrogation of these databases with the Uni-Prot proteome helps to ensure that assignments of our CLT ORF sequences to MS/MS spectra are correct. The PEAKS software, like other MS/MS interrogation software, assigns a probability value (−10lgP; see Table 1) to each spectral assignment to quantify the assignment.

The results of these studies identified numerous individual peptides that were associated with the HLA Class I molecules immunoprecipitated from the 39 lung tumor samples found in the Bulik-Sullivan dataset and the 4 lung squamous cell carcinoma patient samples in the inventors' dataset, that corresponded to the amino acid sequence of CLT-derived ORFs, and did NOT correspond to polypeptide sequences present within the known human proteome (UniProt).

Further manual review of the peptide spectra assigned by the PEAKS software was used to confirm assignment of spectra to peptides that were mapped to 2 CLT-derived ORFs, and thus defined as CLT antigens (Table 1; SEQ ID NOs. 1-2). Interestingly, the patient tumor sample in which the peptide assigned to CLT Antigen 1 was identified was diagnosed as suffering from lung squamous cell carcinoma, whereas the patient tumor sample in which the peptide assigned to CLT Antigen 2 was identified was reported by Bulik-Sullivan et al. to be a non small cell lung cancer patient (see Table 1).

Figure 1:
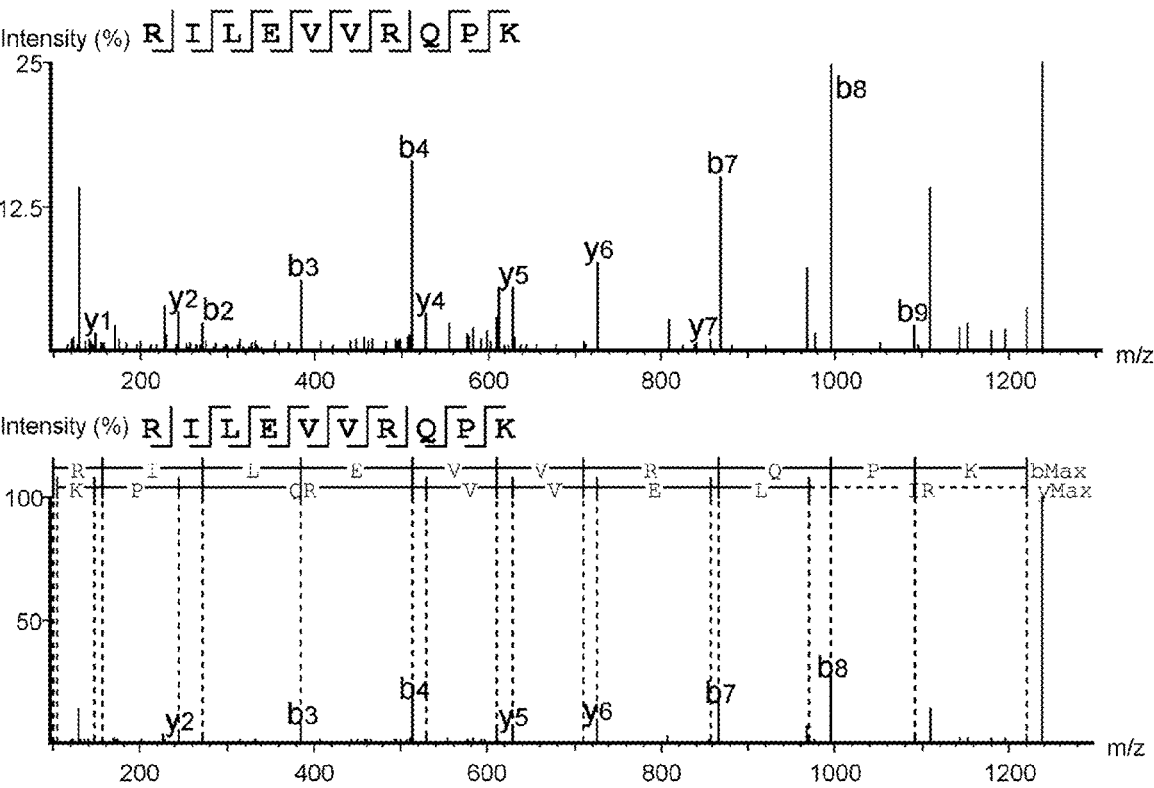
FIG. 1. Spectra for the peptide of SEQ ID NO. 3 isolated from a lung tumor sample of patient LUSCT8.
Figure 2:
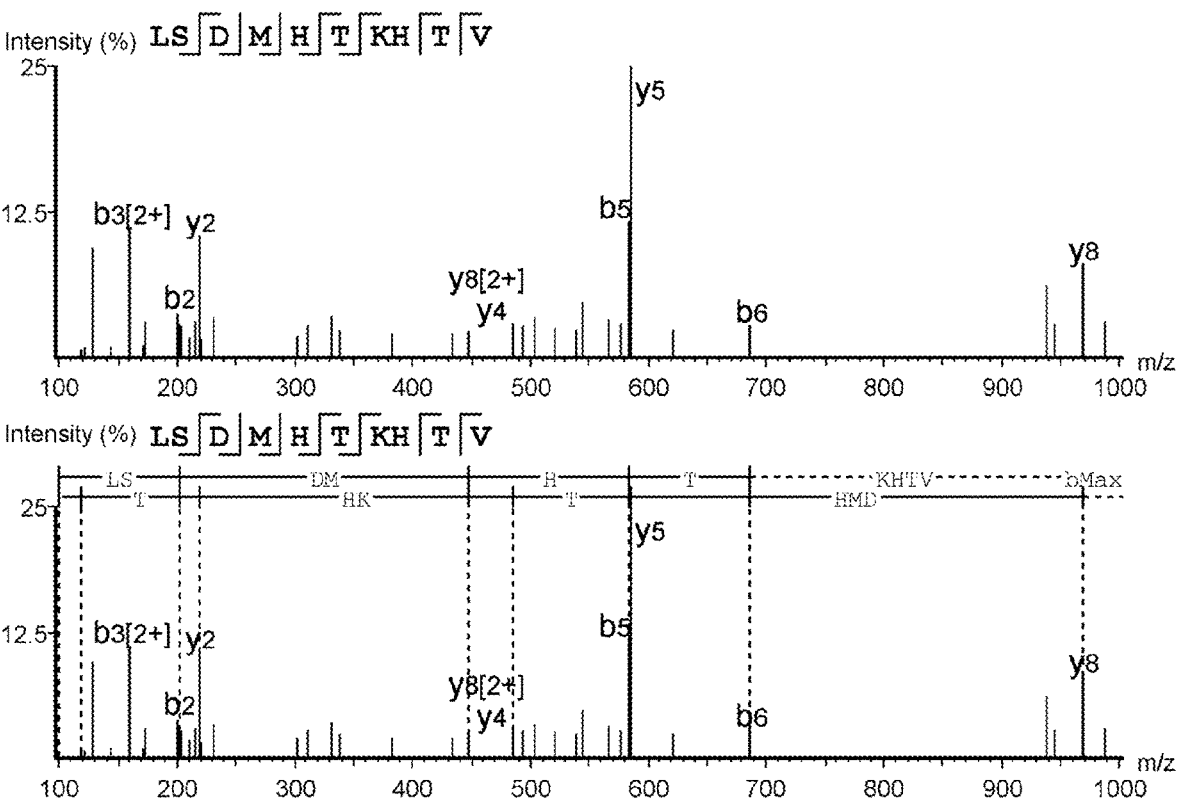
FIG. 2. Spectra for the peptide of SEQ ID NO. 4 isolated from a lung tumor sample of patient train_sample_32.

The discovery of peptides (SEQ 10 NO. 3, 4) associated with the HLA Class molecules found in lung tumor tissues confirms that the 2 ORFs from which they were derived, were first translated in lung tumor tissues, processed through the HLA Class I pathway and finally presented to the immune system in a complex with HLA Class I molecules. Tables 1 shows the properties of the peptides found in the CLT antigens. FIGS. 1-2 show representative MS/MS spectra from each of the lung peptides shown in Table 1. The top panel of each of these figures shows the MS/MS peptide fragment profile, with standard MS/MS annotations (b: N-terminal fragment ion; y: C-terminal fragment ion; $-H_2O$: water loss; $-NH_3$: loss of ammonia; [2+]: doubly charged peptide ion; pre: unfragmented precursor peptide ion; $a_n$-n: internal fragment ion) shown above the most abundant fragment ion peaks assigned by the PEAKS software and obtained from the inventors database or the MassIVE Archive (http://massive.ucsd.edu); accession code MSV000082648. The lower panel of each Figure shows a rendering of the spectrum indicating the positions of the linear peptide sequences that have been mapped to the fragment ions. Consistent with the $-10$lgP scores assigned to the lung peptides in Table 1, the FIGS. 1-2 spectra contain numerous fragments that precisely match the sequences of the peptides (SEQ ID NOs. 3-4) that we discovered in these analyses.

To discover if peptides presented in melanoma tissues were found in our melanoma CLTs, we constructed a database of all predicted polypeptide sequences (ORFs) of ≥10 residues from the 97 cutaneous melanoma CLTs of Example 1, to allow us to interrogate these ORFs with immunopeptidomic data. This yielded 2,269 ORFs ranging in length from 10 to 207 amino acids.

Bassani-Sternberg et al. (Bassani-Sternberg et al., 2016, *Nature Commun.*, 7: 13404; database link: https://www.ebi-.ac.uk/pride/archive/projects/PXD004894) interrogated MS/MS data collected from HLA-bound peptide samples derived from 25 cutaneous melanoma patients against the polypeptide sequences reported for the entire human proteome. These analyses revealed tens of thousands of peptides that matched to known human proteins. As expected, these peptides included peptides found within multiple tumor-associated antigens (TAA), including PRAME, MAGEA3, and TRPM1 (melastatin).

The inventors procured frozen tumor tissue from 4 patients diagnosed with melanoma. Samples between 0.6-1 g were homogenized, the lysate was centrifugate at high speed and the cleared lysate was mixed with protein A (ProA) beads covalently linked to an anti-human HLA class I monoclonal antibody (W6/32). The mixture was incubated overnight at 4° C. to improve HLA Class I molecule binding to antibody (Ternette et al., 2018 *Proteomics* 18, 1700465). The HLA Class I-bound peptides were eluted from the antibody by using 10% acetic acid, and the peptides were then separated from other high molecular mass components using reversed-phase column chromatography (Ternette et al., 2018). The purified, eluted peptides were subjected to nUPLC-MS, and specific peptides of defined charge-to-mass ratio (m/z) were selected within the mass spectrometer, isolated, fragmented, and subjected to a second round of mass spectrometry (MS/MS) to reveal the m/z of the resulting fragment ions (Ternette et al., 2018), producing an MS/MS dataset corresponding to the immunopeptidome for each of these tumor samples.

By applying detailed knowledge of immunopeptidomics evaluation, the inventors interrogated the spectra from the PXD004894 HLA Class I dataset for 25 melanoma patients (Bassani-Sternberg et al., 2016) and the spectra of the HLA-Class I dataset for the 4 melanoma tumors prepared by the inventors with the CLT-derived ORFs (of Example 1), which were concatenated (for each CLT) alongside all polypeptide sequences found in the human proteome (Uni-Prot) using PEAKS™ software (v8.5 and vX, Bioinformatics Solutions Inc). Since the majority of Class I HLA-bound peptides found in cells are derived from constitutively expressed proteins, the simultaneous interrogation of these databases with the UniProt proteome helps to ensure that assignments of our CLT ORF sequences to MS/MS spectra are correct. The PEAKS software, like other MS/MS interrogation software, assigns a probability value ($-10$ lgP, see Table 1) to each spectral assignment to quantify the assignment.

The results of these studies identified >50 individual peptides that were associated with the HLA Class I molecules immunoprecipitated from tumor samples from the 25 patients examined by Bassani-Sternberg et al. and the 4 melanoma patient samples in the inventors' dataset, that corresponding to the amino acid sequence of CLT-derived ORFs, and did NOT correspond to polypeptide sequences present within the known human proteome (UniProt).

Further manual review of the peptide spectra assigned by the PEAKS software was used to confirm assignment of spectra to peptides that were mapped to multiple CLT-derived ORFs, and thus defined as CLT antigens. Interestingly, one of these peptides was identical to one of the peptides discovered in the inventors' interrogation of lung tumor MS/MS datasets (see above) with the ORFeome we created from our lung squamous cell carcinoma CLTs (Table 1; SEQ ID NO. 3). This peptide was discovered in tumors from 3 patients in the Bassani-Sternberg dataset, and one patient from the inventors' melanoma MS/MS dataset (Table 1; SEQ ID NO.3).

Figure 3:
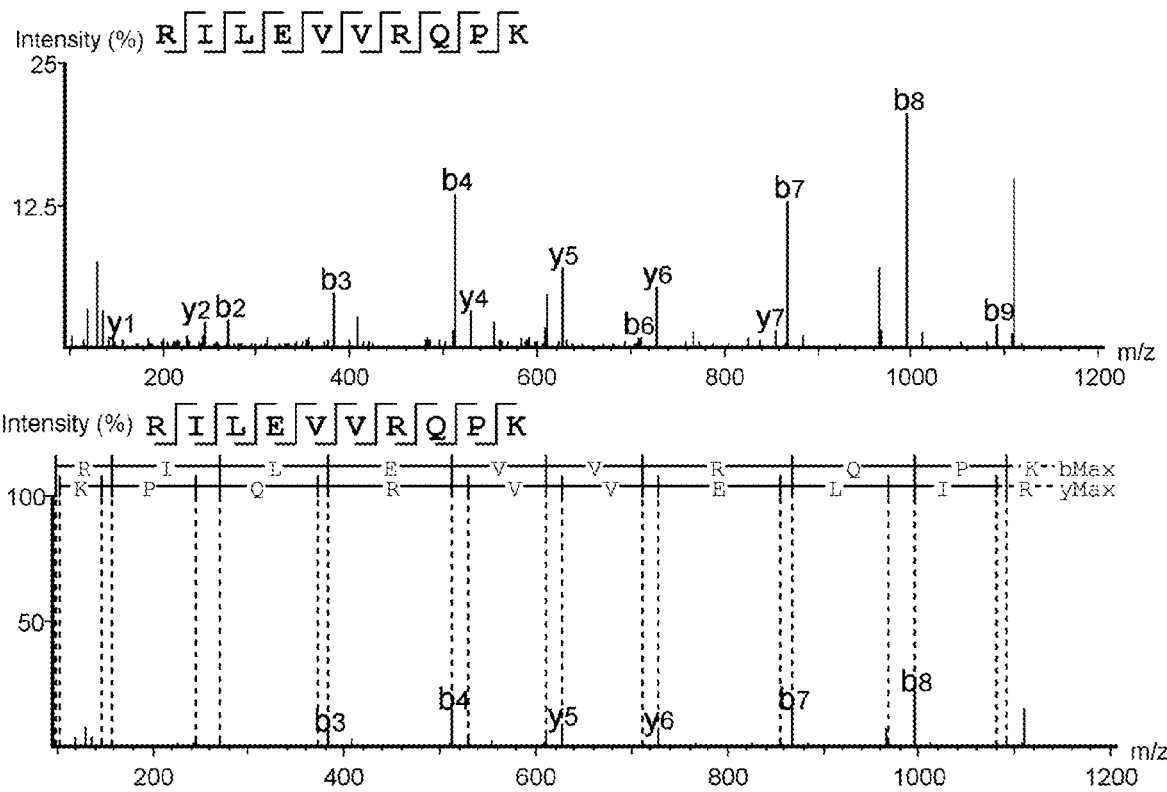
FIG. 3. Spectra for the peptide of SEQ ID NO. 3 isolated from a melanoma tumor samples of patient 2MT3.

The discovery of these peptides associated with the melanoma tissue HLA Class i molecules confirms, that the ORFs from which they were derived, were first translated in melanoma tissues, processed through the HLA Class pathway and finally presented to the immune system in a complex with HLA Class I molecules. Table 1 shows the properties of the peptides (SEQ ID NO. 3, 4) found in the CLT antigens listed in this table. FIG. 3 show representative MS/MS spectra from the peptide for CLT Antigen 1 (SEQ ID NO.1) discovered in melanoma tumors (Table 1, SEQ ID NO. 3). The top panel of this figure shows the MS/MS peptide fragment profile, with standard MS/MS annotations (b: N-terminal fragment ion; y: C-terminal fragment ion; $-H_2O$: water loss; $-NH_3$: loss of ammonia; [2+]: doubly charged peptide ion; pre: unfragmented precursor peptide ion; $a_n$-n: internal fragment ion) shown above the most abundant fragment ion peaks, in an image extracted from the inventors' dataset) by the PEAKS software. The lower panel of each Figure shows a rendering of the spectrum indicating the positions of the linear peptide sequences that have been mapped to the fragment ions. Consistent with the high $-10$ lgP scores assigned to the melanoma peptide in Table 1, the FIG. 3 spectrum contains numerous fragments that precisely match the sequences of the peptide (SEQ ID NO. 3) that we discovered in our analyses of melanoma tissues.

Both of the peptides detected in association with HLA Class I from Table 1 were assessed to determine their predicted strength of binding to HLA Class I molecules reported in their patient of discovery by using the NetMHC-pan 4.0 prediction software (http://www.cbs.dtu.dk/services/NetMHCpan/). These analyses were limited to detections made in the inventors' databases and the Bulik-Sullivan database, since the HLA types of the relevant melanoma patients in the Bassani-Sternberg database were not reported. The results of these prediction studies showed that both peptides (or 9-mers contained within each full sequence) were predicted to bind to at least one of the HLA types found in each of these patients (see Table 2). The fact that both of the detected peptides were expected to bind to HLA types found in the patient in which they were discovered (independent of the tumor type) is consistent with their presentation and MS detection.

To provide further certainty of the assignment of tumor tissue-derived MS spectra to the peptide sequences that we discovered, peptides with these discovered sequences were synthesized and subjected to nUPLC-MS$^2$ using the same conditions applied to the tumor samples obtained by Bulik-Sullivan et al., Bassani-Sternberg et al., or tumor samples obtained by the inventors. Comparison of the spectra for selected peptides are shown in FIGS. 4-6. In each Figure the upper spectrum corresponds to the tumor sample (Bulik-Sullivan et al., or the inventors; same image as shown in top panels of FIGS. 1, 2, 3 respectively) and the lower spectrum corresponds to the synthetically produced peptide of the same sequence. Annotations on these synthetic peptide comparison figures correspond to the annotations described above for the top panel of FIGS. 1-3 (see above). These figures reveal a precise alignment of fragments (tiny differences in the experimentally determined m/z values between tumor- and synthetic peptide-derived fragment ions being well within the m/z tolerances of <0.5 Daltons), confirming the veracity of the assignment of each of the tumor tissue-derived spectra to the CLT-encoded peptides.

Taken together, the peptide data shown in Tables 1 & 2, FIGS. 1-3, and FIGS. 4-6 supply exceptionally strong support for the translation, processing, and presentation of the corresponding CLT antigens in cancer patients.

To further confirm the cancer-specificity of the CLTs, the inventors processed 37 normal tissue samples (5 normal skin, 9 normal lung, 18 normal breast, 6 normal ovary and 5 normal head and neck tissues) and prepared for immuno-peptidomic analysis. The inventors interrogated the spectra of the HLA-Class I dataset from these normal tissue samples, searching for all possible peptide sequences derived from the polypeptide sequences of CLT Antigens 1 and 2. No peptides derived from CLT Antigen 1 or CLT Antigen 2 were detected in the set of normal tissue samples (Table 3) providing additional confirmation that the CLTs have cancer-specific expression.

In summary: the identification of immunopeptidomic peptides derived from the predicted ORFs, demonstrates that these CLTs are translated into polypeptides (SEQ ID NOs. 1-2; referred to as CLT antigens) in tumor tissue. These are then processed by the immune surveillance apparatus of the cells, and component peptides are loaded onto HLA Class I molecules, enabling the cell to be targeted for cytolysis by T cells that recognize the resulting peptide/HLA Class I complexes. Thus, CLT Antigen 1 (SEQ ID NO.1) and fragments thereof are expected to be useful in a variety of therapeutic modalities for the treatment of non small cell lung cancer and melanoma patients whose tumors express these antigens, and CLT Antigen 2 (SEQ ID NO.2) and fragments thereof are expected to be useful in a variety of therapeutic modalities for the treatment of non small cell lung cancer patients whose tumors express these antigens.

TABLE 1

List of peptides identified by immunopeptidomic analyses of lung tumor samples, along with CLT antigen name and cross reference to SEQ ID NOs.

| Peptide Sequence[1] | Peptide SEQ ID NO. | CLT Ant. NO. | CLT Ant. SEQ ID NO. | Patient[2] | Patient disease[2] | Peptide mass[3] | Peptide length | -10lgP[4] | # of Spectra[5] | Ppm[6] |
|---|---|---|---|---|---|---|---|---|---|---|
| RILEVV RQPK | SEQ ID NO. 3 | 1 | SEQ ID NO. 1 | LUSCT 8 | Lung Squamous cell carcinoma | 1236.7666 | 10 | 42.72 | 1 | 0.9 |
| RILEVV RQPK | SEQ ID NO. 3 | 1 | SEQ ID NO. 1 | 2MT3 | Melanoma | 1236.7666 | 10 | 48.84 | 4 | 1.1 |
| RILEVV RQPK | SEQ ID NO. 3 | 1 | SEQ ID NO. 1 | Mel39 | Melanoma | 1236.7666 | 10 | 41.42 | 2 | 1.5 |
| RILEVV RQPK | SEQ ID NO. 3 | 1 | SEQ ID NO. 1 | Mel4 | Melanoma | 1236.7666 | 10 | 31.5 | 2 | 3.1 |
| RILEVV RQPK | SEQ ID NO. 3 | 1 | SEQ ID NO. 1 | Mel36 | Melanoma | 1236.7666 | 10 | 39.91 | 2 | 1.8 |

TABLE 1-continued

List of peptides identified by immunopeptidomic analyses of lung tumor
samples, along with CLT antigen name and cross reference to SEQ ID NOs.

| Peptide Sequence[1] | Peptide SEQ ID NO. | CLT Ant. NO. | CLT Ant. SEQ ID NO. | Patient[2] | Patient disease[2] | Peptide mass[3] | Peptide length | -10lgP[4] | # of Spectra[5] | Ppm[6] |
|---|---|---|---|---|---|---|---|---|---|---|
| LSDMHT KHTV | SEQ ID NO. 4 | 2 | SEQ ID NO. 2 | train_ sample_ 32 | NSCLC | 1167.5707 | 10 | 17.49 | 1 | 5 |

[1]HLA Class I peptides identified by mass spectrometry.
[2]Inventors' MS/MS database for Lung squamous cell lung cancer (LUSCT8), Inventors' MS/MS database for melanoma (2MT3), Bassani-Sternberg et al. database for melanoma (Mel4, Mel36, Mel39), Bulik-Sullivan et al., database for lung cancer (train_sample_32).
[3]Calculated peptide mass.
[4]PEAKS™ program-10lgP values.
[5]Number of spectra in which peptide was detected.
[6]Deviation between observed mass and calculated mass.

20

| Peptide sequence[1] | Patient[2] | Tumor type | Predicted to bind at least 1 reported HLA type with a Rank score of ≤5.0%[3] | Number of patient alleles predicted to bind with a rank score of ≤5.0%[4] | Number of patient alleles predicted to bind with a rank score of ≤2.0%[5] | Peptide SEQ ID NO. | CLT Antigen NO. |
|---|---|---|---|---|---|---|---|
| RILEWRQ PK | LUSCT8 | LUSC | YES | 2 | 2 | SEQ ID NO. 3 | 1 |
| RILEWRQ PK | 2MT3 | melanoma | YES | 1 | 1 | SEQ ID NO. 3 | 1 |
| LSDMHT KHTV | train_ sample_ 32 | NSCLC | YES | 1 | 1 | SEQ ID NO. 4 | 2 |

[1]HLA Class I peptides identified by mass spectrometry.
[2]Inventors' MS/MS database for Lung squamous cell lung cancer (LUSCT8), Inventors' MS/MS database for melanoma (2MT3), Bulik-Sullivan et al., database for lung cancer (train-sample_32).
[3]Predicted binding to patient's reported HLA Class I types at a Rank score of ≤5.0%.
[4]Number of patient HLA Class I types predicted to bind with a Rank score of ≤5.0%.
[5]Number of patient HLA Class I types predicted to bind with a Rank score of ≤2.0%.

TABLE 3

Number of peptides-derived from CLT Antigens
1 to 2 in a set of normal tissue samples.

| Antigen | Skin | Lung | Breast | Ovary | Head and Neck |
|---|---|---|---|---|---|
| CLT Antigen 1 | 0/5 | 0/9 | 0/18 | 0/6 | 0/5 |
| CLT Antigen 2 | 0/5 | 0/9 | 0/18 | 0/6 | 0/5 |

The results presented here in Examples 1 and 2 are in whole or part based upon data generated by the The Cancer Genome Atlas (TCGA) Research Network (http://cancergenome.nih.gov/) and the Genotype-Tissue Expression (GTEx) Project (supported by the Common Fund of the Office of the Director of the National Institutes of Health, and by NCI, NHGRI, NHLBI, NIDA, NIMH, and NINDS).

Example 3—Assays to Demonstrate T Cell Specificity for CLT Antigens in Lung Cancer Patients (a) Staining Reactive T Cells with CLT Antigen Peptide Pentamers The presence and activity of circulating CD8 T cells specific for CLT antigens in lung cancer patients and/or melanoma patients can be measured by using HLA Class 1/peptide-pentamer ("pentamer") staining and/or in vitro killing assays. Thus, application of these methodologies to CLT antigens discovered using the methods elucidated in Examples 1 & 2 (Table 1 and 2, FIGS. 1-6) can be used to demonstrate the existence of therapeutically relevant T cell responses to the CLT antigens in cancer patients.

For these studies, CD8 T cells isolated from patient blood are expanded using various cultivation methods, for example anti-CD3 and anti-CD28 coated microscopic beads plus Interleukin-2. Expanded cells can then be stained for specific CLT antigen-reactivity of their T cell receptors using CLT peptide pentamers, which consist of pentamers of HLA Class I molecules bound to the relevant CLT Antigen peptide in the peptide-binding groove of the HLA molecule. Binding is measured by detection with phycoerythrin or allophyco-cyanin-conjugated antibody fragments specific for the coiled-coil multimerisation domain of the pentamer structure. In addition to the pentamer stain, further surface markers can be interrogated such as the memory marker CD45RO and the lysosomal release marker CD107a. Association of pentamer positivity with specific surface markers can be used to infer both the number and state (memory versus naive/stem) of the pentamer-reactive T cell populations Pentamer stained cells may also be sorted and purified using a fluorescence activated cell sorter (FACS). Sorted cells may then be further tested for their ability to kill target cells in in vitro killing assays. These assays comprise a CD8 T cell population, and a fluorescently labelled target cell population. In this case, the CD8 population is either CLT antigen-specific or CD8 T cells pentamer-sorted and specific for a positive-control antigen known to induce a strong killing response such as Mart-1. The target cells for these studies may include peptide-pulsed T2 cells which express HLA-A*02, peptide-pulsed Cl R cells transfected with HLA-A*02,03 or B*07 or lung cancer cells lines and/or melanoma cell lines previously shown to express the CLTs/CLT antigens, or patient tumor cells. Peptides used to pulse the T2 or Cl R cells include CLT antigen peptides or positive control peptides. Target cells may be doubly labelled with vital dyes, such as the red nuclear dye nuclight rapid red which is taken up into the nucleus of healthy cells. Additional evidence of target cell attack by specific T cells may be demonstrated by green caspase 3/7 activity indicators that demonstrate caspase 3/7-mediated apoptosis. In this way, as target cells are killed, by apoptosis mediated by CD8 T cells, they lose their red fluorescence and gain green fluorescence due to the caspase 3/7 activity intrinsic to apoptosis. Thus, application of such killing assays to pentamer-sorted, CLT antigen-specific CD8 T cells can be used to enumerate the cytotoxic activity of CLT-antigen-specific T cells in ex vivo cultures of lung cancer and/or melanoma patient T cells.

(b) HERVfest Analyses of T Cell Specificity in Lung Cancer Patients

Functional expansion of specific T cells (fest) technology has been used identify specific tumor-derived epitopes present in the "mutation-associated neoantigen" (MANA) repertoire found in tumor cells of patients who have responded to checkpoint-blockade therapies (Anagnostou et al., Cancer Discovery 2017; Le et al., Science 2017). Application of this technology to CLT antigens discovered using the methods elucidated in Example 1 & 2 (Table 1 and 2, FIGS. 1-31) can confirm the existence of therapeutically relevant T cell responses to the CLT antigens in cancer patients.

Like other assays (e.g., ELISPOT) to identify epitope-specific T cells in a subject who has undergone immune exposure, "fest" technologies derive their specificity by expanding the cognate T cells in ex vivo cultures that include antigen-presenting cells and suitable antigenic peptides. The technique differs from other immunological assays in that it utilizes next-generation sequencing of the T cell receptor (TCR) mRNA present in these amplified cultures (specifically: TCRseq targeting the TCR-Vβ CDR3 region) to detect the specific TCRs that are expanded in the cells cultured with the target peptides (preselected to match the HLA type of the patient, using standard HLA-binding algorithms). Application of TCRseq to tumor tissues in the same patient, harvested after successful checkpoint-blockade therapy, can then be used to determine which TCRs/T cells detected in the ex vivo, peptide-stimulated cultures, are also present at the site of immune-suppression of the cancer. In the case of MANAfest, the method is used to identify specific TCRs that recognize MHC-presented neoantigen peptides that evolve in each patient's tumor and are also detected in the T cells in the patients' tumors, permitting the identification of the functionally relevant neoantigens peptides among the thousands of possible mutant peptides found by full-exome sequencing of normal and tumor tissues from each patient (Le et al., Science 2017).

Application of MANAfest (Anagnostou et al., 2017 Cancer Discovery) technology to CLT antigens is done as follows. Step 1: Peptides predicted to contain epitopes that efficiently bind selected HLA supertypes are identified in CLT antigens. Step 2: PBMCs from appropriate patients are selected, and matched by HLA type to the peptide library selected in step 1. Step 4: PBMCs from these patients are separated into T cell and non-T cell fractions. Non-T cells are irradiated (to prevent proliferation), added back to the patient's T cells, and then divided into 20-50 samples, and cultivated in T cell growth factors and individual CLT-specific synthetic peptides (selected in step 1) for 10 to 14 days. Step 4: TCRseq (sequencing of the epitope-specific TCR-Vβ CDR3 sequences) is performed on all wells to identify the cognate T cells/TCRs that have been amplified in the presence of the test peptides; specificity of these TCRs is determined by comparison to TCRs detected in unamplified/propagated T cells using TCRseq. Data obtained from this step can confirm which peptides elicited an immune response in the patient. Step 5: TCRseq is performed on tumor samples to determine which of the specifically amplified TCRs homed to the tumor of patients who have responded to checkpoint-blockade therapy, providing evidence that T cells bearing this TCRs may contribute to the effectiveness of the checkpoint blockade therapy.

Example 4—Assays to Demonstrate High-Affinity T Cells Specific for CLT Antigens have not Been Deleted from Normal Subjects' T Cell Repertoire An ELISPOT assay may be used to show that CLT antigen-specific CD8 T cells are present in the normal T cell repertoire of healthy individuals, and thus have not been deleted by central tolerance due to the expression of cancer-specific CLT antigens in naïve and thymic tissues in these patients. This type of ELISPOT assay comprises multiple steps. Step 1: CD8 T cells and CD14 monocytes can be isolated from the peripheral blood of normal blood donors, these cells are HLA typed to match the specific CLT antigens being tested. CD8 T cells can be further sub-divided into naïve and memory sub-types using magnetically labelled antibodies to the memory marker CD45RO. Step 2: CD14 monocytes are pulsed with individual or pooled CLT antigen peptides for three hours prior to being co-cultured with CD8 T cells for 14 days. Step 3: Expanded CD8 T cells are isolated from these cultures and re-stimulated overnight with fresh monocytes pulsed with peptides. These peptides may include; individual CLT antigen peptides, irrelevant control peptides or peptides known to elicit a robust response to infectious (e.g., CMV, EBV, Flu, HCV) or self (e.g. Mart-1) antigens. Re-stimulation is performed on anti-Interferon gamma (IFNγ) antibody-coated plates. The antibody captures any IFNγ secreted by the peptide-stimulated T cells. Following overnight activation, the cells are washed from the plate and IFNγ captured on the plate is detected with further anti-IFNγ antibodies and standard colorimetric dyes. Where IFNγ-producing cells were originally on the plate, dark spots are left behind. Data derived from such assays includes spot count, median spot size and median spot intensity. These are measures of frequency of T cells producing IFNγ and amount of IFNγ per cell. Additionally, a measure of the magnitude of the response to the CLT antigen can be derived from the stimulation index (SI) which is the specific response, measured in spot count or median spot size, divided by the background response to monocytes with no specific peptide. In this way, comparisons of the responses to CLT antigens and control antigens can be used to demonstrate that naïve subjects contain a robust repertoire of CLT antigen-reactive T-cells that can be expanded by vaccination with CLT antigen-based immunogenic formulations.

Example 5—qRT-PCR Validation of CLT Expression in Melanoma Cell Lines

Quantiative real-time polymerase chain reaction (qRT-PCR) is a widespread technique to determine the amount of a particular transcript present in RNA extracted from a given biological sample. Specific nucleic acid primer sequences are designed against the transcript of interest, and the region between the primers is subeqeuntly amplified through a series of thermocyle reactions and fluorescently quantified through the use of intercalating dyes (SYBR Green). Primer pairs were designed against the CLTs and assayed against RNA extracted from melanoma cell lines. Non-melanoma cell lines were utilised as negative controls. Specifically, melanoma cell lines COLO 829 (ATCC reference CRL-1974), MeWo (ATCC reference HTB-65), SH-4 (ATCC reference CRL-7724) and control cell lines HepG2 (hepatocellular carcinoma, ATCC reference HB-8065), Jurkat (T-cell leukemia, ATCC reference T1B152) and MCF7 (adenocarcinoma, ATCC reference HTB-22) were expanded in vitro and RNA was extracted from $1 \times 10^6$ snap-frozen cells and reverse transcribed into cDNA. qRT-PCR analysis WITH SYBR Green detection following standard techniques was performed with primers designed against two regions of each CLT, and reference genes. Relative quantification (RQ) was calculated as:

$$RQ = 2[Ct(REFERENCE) - Ct(TARGET)].$$

The results of these experiments are presented in FIG. 7, which shows results from a qRT-PCR assay with two primer sets (72+73 and 74+75) targeting the CLT encoding CLT Antigen 1 (SEQ ID NO. 5) on RNA extracted from three melanoma cell lines and three non-melanoma cell lines. These results confirmed the specific expression of the CLT in RNA extracted from melanoma cell lines, compared to non-melanoma cells. The CLT was detected in ⅔ of the melanoma cell lines tested.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps. All patents, patent applications and references mentioned throughout the specification of the present invention are herein incorporated in their entirety by reference. The invention embraces all combinations of preferred and more preferred groups and suitable and more suitable groups and embodiments of groups recited above.

SEQUENCE LISTING
(Polypeptide sequence of CLT Antigen 1)
                                SEQ ID NO. 1
MGQLNNLISIMSSSRILEVVRQPKWKGSRRGILVLPITHM (Polypeptide sequence of CLT Antigen 2)
                                SEQ ID NO. 2
MPCPASAHTRCVHPLTCAHCLALPSEMHPVPQMEM

QKSPVFCVAHAGSCRPELFLFSHLGSSSQSTILFS

LLILSDMHTKHTVDLENG (peptide sequence derived from CLT Antigen 1)
                                SEQ ID NO. 3
RILEVVRQPK (peptide sequence derived from CLT Antigen 2)
                                SEQ ID NO. 4
LSDMHTKHTV (cDNA sequence of CLT encoding CLT Antigen 1)
                                SEQ ID NO. 5
GAAAGACAGCATTCAAGGAACCACCTTGTACGCAG

ACACTGAAACCTCGCGAGACAACAAAACTGCTGAC

ACCTTGATCTTGGACTTCCCAGCCTCCAGAACTAT

AAACCAGCAAAGAGTACATAGAACAAACATTTTTT

TTAGAAGGATTAAATGGGACAATTAAACAATTTGA

TCAGCATAATGTCCAGCTCAAGGATCTTGGAGGTG

GTGAGGCAGCCCAAGTGGAAAGGCAGCAGAAGGGG

TATCCTTGTTTTACCAATTACTCATATGTAGGAGA

TGGTGCATTAAATGAAATATTCTCTGCTCTCTCCT

AACATCTACCCCCTCACACCAAGAGGAAGGCATGT

CGCCTGAACCTTTGCAGTATTCAATTAAAGTTCTA

TTCACACGGT (cDNA sequence of CLT encoding CLT Antigen 2)
                                SEQ ID NO. 6
TTCGAGCTTCCCAGCTGCTTTGTTTACCTAAGCAA

GCCTGGGCAATGGTGGGCGTCCCTCCCCCAGCCTC

GCTGCCGCCTTGCAGTTTGATCTCAGACTGCTGTG

CTAGCAATCAGCGAGACTCCGTGGGCGTAGGACCC

TCCGAGCCAGGTGCGGGATATAATCTTGTGGTGCG

CTGTTTTTTAAGCCGGTCGGAAAAGCGCAGTATTC

GGGTGGGAGTGACCTGATTTTCCAGGTGCGTCCGT

CACCCCTTTCTTTGACTCGGAAAGGGAACTCCCTG

ACCCCTTGCGCTTCCCAAGTGAGGCAATGCCTTGC

CCGGCTTCGGCTCACACACGGTGTGTGCACCCACT

GACCTGCGCCCACTGTCTGGCACTCCCTAGTGAGA

TGCACCCGGTACCTCAGATGGAAATGCAGAAATCA

CCCGTCTTCTGCGTCGCTCACGCTGGGAGCTGTAG

ACCGGAGCTGTTCCTATTCAGCCATCTTGGCTCCT

CCTCCCAGTCCACCATTCTTTTCAGCTTGCTGATT

CTGAGTGATATGCATACAAAGCATACAGTTGACTT

-continued

GGAAAATGGCTGAAGCCCTCACTGGGGGAAACATC

AAAGGAATACTCACTGTTTATACTTGAAGTGAACC

AACATCAACTTGAATCAATGGATTTTGGGTCTGTG

GACTGACTCAGATCTAGAAACTGCACGAAGAAGAG

CAATTTTGCATGTGGCATCTGATATCAACCTTCTG

ATAACCAAGAGCTAGTTTTTAATCATAATAAAATT

GAAGAATAGCAAGTTGACTACCCATCTATCTTACC

CCTGAGAACACCATGGCCTGTTTTCAGTTGTCATA

GATTCCTGGGCAGTAAGACATTGTGATTTCCATTC

CAGCCTTGCTGCACATCATATTAATTATGGTTAAG

GGCTCAGTGTTGCCATGTGGCCTCTGGCATTCCAG

AATCTCAACATCCACATTGATATTATACAGCCCAG

TTCCATGGAAGAATAGAGCATTGACCCCAATCTAC

AGACAGCAGCCACTGCTAAGCCTCTCAAAGATACT

AGTGTTTCCATCACTAGCACATTACTTAATAGAGT

GCCTTTCGTTGCTCCTTGTATACATGGATGTACAG

TCAGTTGATGGGTTTTCACGTCTTGCACTGTAATT

CAATGCTAATCCCTTAAACTTACTTTTTTGTACTA

TGTCAAGACAGTTCGGGTATCTCTACCTGGGTTAC

AGTAGGCTATCAACCTTCACGGAGCCATCCCAAGC

AAATATTAGCACTGGCTCTAGGTAGCCTTGCCAGA

ATGTTAAATTTCAGTTAAGTATGCTAAATGAATGT

GATAACTTTATGCAACTTTTCATCCATGACTTTCT

TTTAGTGTAAAGGAGCAATTGATTATTAGGACAAC

TGATTAACTCTGGTTAAGGTGAATAGATTTACTAA

-continued

AAACATTGTATTAATGTTAATATTCTCATTTTGTT

TTAATTGTGCTATAATTGTGTAAGAGAATGACTTT

GATTTTAGGAAATATACACTGAAGTATTTAGGGTT

AAATGGTATTATGTCTCCAACTTAATCTCAGGCAG

TTAAGAAAAATTAATGTGCATGTGTGTGTGTAGGG

AAAGAAAGAGGGAGGAAAGGAGGAATAGAGAGGAA

GAGAGAGGGTAAATGATAAAGCAATGTGGTAAAAA

CATTAACATTCTAACATATTGGGAATCTGGAGATT

CTCTGTACCATTTTCCAACCCATGTTAAGTGTGAA

ATTACGTCAAAGT (cDNA sequence encoding CLT Antigen 1)

SEQ ID NO. 7

ATGGGACAATTAAACAATTTGATCAGCATAATGTC

CAGCTCAAGGATCTTGGAGGTGGTGAGGCAGCCCA

AGTGGAAAGGCAGCAGAAGGGGTATCCTTGTTTTA

CCAATTACTCATATGTAG (cDNA sequence encoding CLT Antigen 2)

SEQ ID NO. 8

ATGCCTTGCCCGGCTTCGGCTCACACACGGTGTGT

GCACCCACTGACCTGCGCCCACTGTCTGGCACTCC

CTAGTGAGATGCACCCGGTACCTCAGATGGAAATG

CAGAAATCACCCGTCTTCTGCGTCGCTCACGCTGG

GAGCTGTAGACCGGAGCTGTTCCTATTCAGCCATC

TTGGCTCCTCCTCCCAGTCCACCATTCTTTTCAGC

TTGCTGATTCTGAGTGATATGCATACAAAGCATAC

AGTTGACTTGGAAAATGGCTGA

The invention claimed is:

1. A composition comprising an isolated polypeptide and an immunostimulant, wherein:
  (a) the isolated polypeptide consists of an amino acid sequence comprising at least 9 contiguous residues of SEQ ID NO: 1 or 2;
  (b) the isolated polypeptide comprises an amino acid sequence having at least 90% identity over the entire length of SEQ ID NO: 1 or 2;
  (c) the isolated polypeptide comprises an amino acid sequence selected from the group consisting of SEQ ID NOs: 1-4; or
  (d) the amino acid sequence of the isolated polypeptide consists of an amino acid sequence selected from the group consisting of SEQ ID NOs: 1-4.

2. The composition of claim 1, wherein the immunostimulant is selected from the group consisting of aluminum salts, saponins, immunostimulatory oligonucleotides, oil-in-water emulsions, aminoalkyl glucosaminide 4-phosphates, lipopolysaccharides and derivatives thereof, TLR4 ligands, TLR7 ligands, TLR8 ligands, TLR9 ligands, IL-12, and interferons.

3. A fusion protein comprising a first polypeptide and one or more additional polypeptides, wherein the first polypeptide:
  (a) consists of an amino acid sequence comprising at least 9 contiguous residues of SEQ ID NO: 1 or 2;
  (b) comprises an amino acid sequence having at least 90% identity over the entire length of SEQ ID NO: 1 or 2;
  (c) comprises an amino acid sequence selected from the group consisting of SEQ ID NOs: 1-4; or
  (d) consists of an amino acid sequence selected from the group consisting of SEQ ID NOS: 1-4.

4. An isolated antigen-binding polypeptide which is immunospecific for a polypeptide as set forth in claim 1, optionally wherein the antigen-binding polypeptide is an antibody or a T cell receptor, or an antigen-binding fragment of any one thereof.

5. A vector or artificial nucleic acid sequence encoding a polypeptide, wherein the polypeptide:
  (a) consists of an amino acid sequence comprising at least 9 contiguous residues of SEQ ID NO: 1 or 2;
  (b) comprises an amino acid sequence having at least 90% identity over the entire length of SEQ ID NO: 1 or 2;
  (c) comprises the amino acid sequence of SEQ ID NO: 1 or 2; or
  (d) consists of an amino acid sequence selected from the group consisting of SEQ ID NOS: 1-4.

6. The artificial nucleic acid sequence of claim 5, wherein the artificial nucleic acid is mRNA.

7. A method of preparing a T-cell population comprising stimulating and amplifying T-cells ex vivo using a polypeptide as set forth in claim 1.

8. A T-cell population obtained by the method of claim 7.

9. A method of preparing an antigen presenting cell population, comprising introducing into antigen presenting cell ex vivo a polypeptide as set forth in claim 1, or a nucleic acid sequence encoding the polypeptide.

10. An antigen presenting cell population obtained by the method of claim 9.

11. An exosome comprising a polypeptide or a nucleic acid sequence encoding the polypeptide, wherein the polypeptide:
  (a) comprises an amino acid sequence comprising at least 9 contiguous residues of SEQ ID NO: 1 or 2;
  (b) comprises an amino acid sequence having at least 90% identity over the entire length of SEQ ID NO: 1 or 2;
  (c) comprises an amino acid sequence selected from the group consisting of SEQ ID NOs: 1-4; or
  (d) consists of an amino acid sequence selected from the group consisting of SEQ ID NOS: 1-4.

12. A method of stimulating an immune response in a subject, the method comprising administering to the subject a therapeutically effective amount of a polypeptide as set forth in claim 1, or a nucleic acid sequence encoding the polypeptide.

13. A method of stimulating an immune response in a subject, the method comprising administering to the subject a therapeutically effective amount of the T-cell population of claim 8.

14. A method of stimulating an immune response in a subject, the method comprising administering to the subject a therapeutically effective amount of the antigen presenting cell population of claim 10.

15. A method of treating a subject suffering from a cancer expressing a polypeptide comprising the amino acid sequence of SEQ ID NO: 1 or 2, or an immunogenic fragment or variant thereof, the method comprising administering to the subject a therapeutically effective amount of a polypeptide as set forth in claim 1, or a nucleic acid sequence encoding the polypeptide.

16. A method of treating a subject suffering from a cancer expressing a polypeptide comprising the amino acid sequence of SEQ ID NO: 1 or 2, or an immunogenic fragment or variant thereof, the method comprising administering to the subject a therapeutically effective amount of the T-cell population of claim 8.

17. A method of treating a subject suffering from a cancer expressing a polypeptide comprising the amino acid sequence of SEQ ID NO: 1 or 2, or an immunogenic fragment or variant thereof, the method comprising administering to the subject a therapeutically effective amount of the antigen presenting cell population of claim 10.

18. A method of diagnosing a subject as suffering from a cancer, the method comprising determining if cells of the subject comprise a polypeptide comprising the amino acid sequence of SEQ ID NO: 1 or 2, or an immunogenic fragment or variant thereof, or a nucleic acid sequence expressing the polypeptide, wherein the presence of the polypeptide or nucleic acid sequence in the cells indicates that the subject has cancer.

19. A method of making the composition of claim 1, the method comprising combining an immunostimulant with an isolated polypeptide, wherein:
  (a) the isolated polypeptide consists of an amino acid sequence comprising at least 9 contiguous residues of SEQ ID NO: 1 or 2;

(b) the isolated polypeptide comprises an amino acid sequence having at least 90% identity over the entire length of SEQ ID NO: 1 or 2;

(c) the isolated polypeptide comprises an amino acid sequence selected from the group consisting of SEQ ID NOs: 1-4; or (d) the amino acid sequence of the isolated polypeptide consists of an amino acid sequence selected from the group consisting of SEQ ID NOs: 1-4.

20. An isolated peptide:

(i) comprising an amino acid sequence selected from the group consisting of SEQ ID NO: 1 and 2;

(ii) consisting of an amino acid sequence selected from the group consisting of SEQ ID NOs: 1-4; or a salt thereof, and/or a composition thereof.

\*    \*    \*    \*    \*